US011964091B1

(12) United States Patent
Fischell et al.

(10) Patent No.: US 11,964,091 B1
(45) Date of Patent: Apr. 23, 2024

(54) METHOD AND APPARATUS FOR CATHETER-BASED EXTRACORPOREAL MEMBRANE OXYGENATION (ECMO)

(71) Applicant: Vantis Vascular, Inc., Kalamazoo, MI (US)

(72) Inventors: Tim A. Fischell, Kalamazoo, MI (US); Frank Saltiel, Kalamazoo, MI (US); Jeffrey Payne, Temecula, CA (US)

(73) Assignee: Vantis Vascular, Inc., Kalamazoo, MI (US)

( * ) Notice: Subject to any disclaimer, the term of this patent is extended or adjusted under 35 U.S.C. 154(b) by 0 days.

(21) Appl. No.: 18/484,398

(22) Filed: Oct. 10, 2023

(51) Int. Cl.
*A61M 1/36* (2006.01)
*A61M 1/16* (2006.01)
*A61M 25/10* (2013.01)
*A61M 25/00* (2006.01)

(52) U.S. Cl.
CPC ........ *A61M 1/3659* (2014.02); *A61M 1/1698* (2013.01); *A61M 1/3666* (2013.01); *A61M 25/10* (2013.01); *A61M 2025/0004* (2013.01); *A61M 2025/0031* (2013.01); *A61M 2210/125* (2013.01)

(58) Field of Classification Search
CPC .............. A61M 1/3659; A61M 1/3661; A61M 1/1698; A61M 1/3666; A61M 25/10; A61M 25/1006; A61M 2025/0004; A61M 2025/0031; A61M 2210/125
See application file for complete search history.

(56) References Cited

U.S. PATENT DOCUMENTS

| 6,709,418 B1 * | 3/2004 | Aboul-Hosn | ....... A61M 1/3667 604/167.03 |
| 6,814,713 B2 * | 11/2004 | Aboul-Hosn | ...... A61B 17/3496 604/107 |
| 8,591,460 B2 * | 11/2013 | Wilson | .............. A61M 25/0141 604/95.04 |
| 10,307,575 B2 * | 6/2019 | Alaswad | ............. A61M 60/857 |
| 11,491,313 B2 | 11/2022 | Fischell et al. | |
| 11,759,315 B1 | 9/2023 | Fischell et al. | |
| 11,766,328 B1 * | 9/2023 | Fischell | ................. A61N 1/056 623/2.11 |
| 2009/0112050 A1 * | 4/2009 | Farnan | ................ A61M 1/3666 606/151 |

(Continued)

FOREIGN PATENT DOCUMENTS

WO WO2021/167653 A1 8/2021
WO WO2022/271999 A1 12/2022

OTHER PUBLICATIONS

Fischell et al.; U.S. Appl. No. 18/448,888 entitled "Method and apparatus for antegrade transcatheter valve repair or implantation," filed Aug. 11, 2023.

*Primary Examiner* — Philip R Wiest
(74) *Attorney, Agent, or Firm* — Shay Glenn LLP

(57) ABSTRACT

A method and system for performing transseptal extracorporeal membrane oxygenation is disclosed. The method may include puncturing a septum between the right atrium and the left atrium and advancing a catheter system through the puncture and into the aorta. A first portion of the catheter system can remove blood from the patient, in some examples near the inferior vena cava. A second portion can return oxygenated blood to the patient, through the transseptal puncture and into the aorta.

19 Claims, 23 Drawing Sheets

(56) References Cited

U.S. PATENT DOCUMENTS

| | | | |
|---|---|---|---|
| 2009/0149950 A1* | 6/2009 | Wampler | A61M 60/178 623/3.13 |
| 2010/0331939 A1* | 12/2010 | Elencwajg | A61N 1/056 607/122 |
| 2016/0082176 A1* | 3/2016 | Kelly | A61M 60/38 600/16 |
| 2019/0255299 A1 | 8/2019 | Fischell et al. | |
| 2019/0307996 A1* | 10/2019 | Alaswad | A61M 60/216 |
| 2020/0179661 A1 | 6/2020 | Fischell et al. | |
| 2020/0409239 A1 | 12/2020 | Ito | |
| 2022/0047303 A1 | 2/2022 | Willis et al. | |

\* cited by examiner

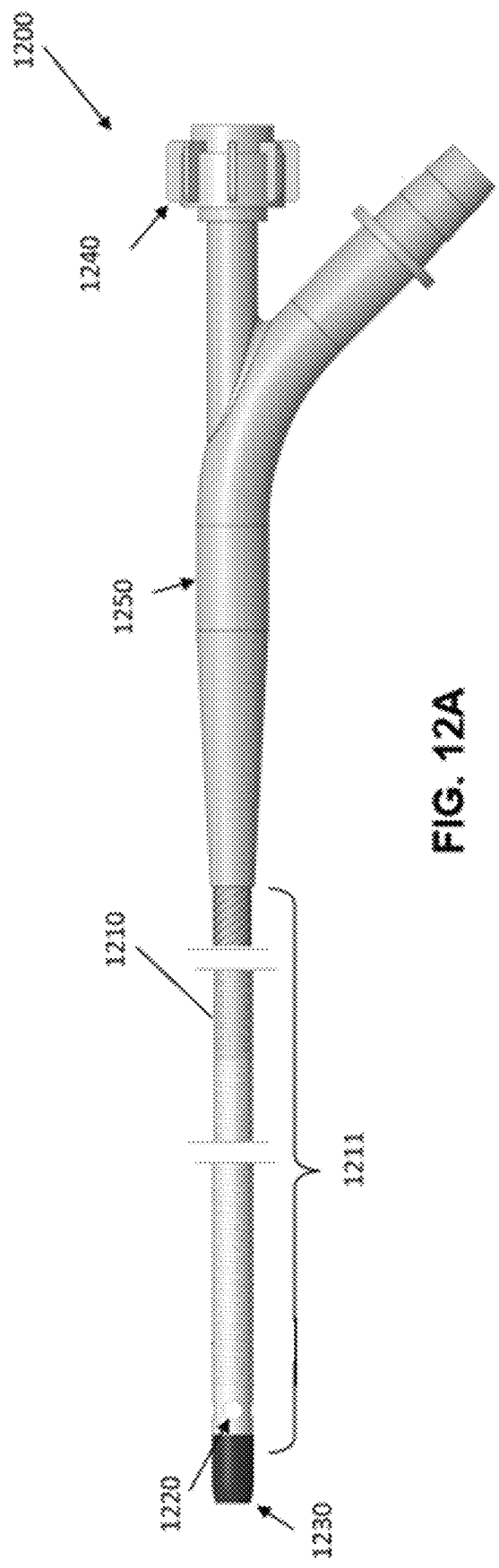
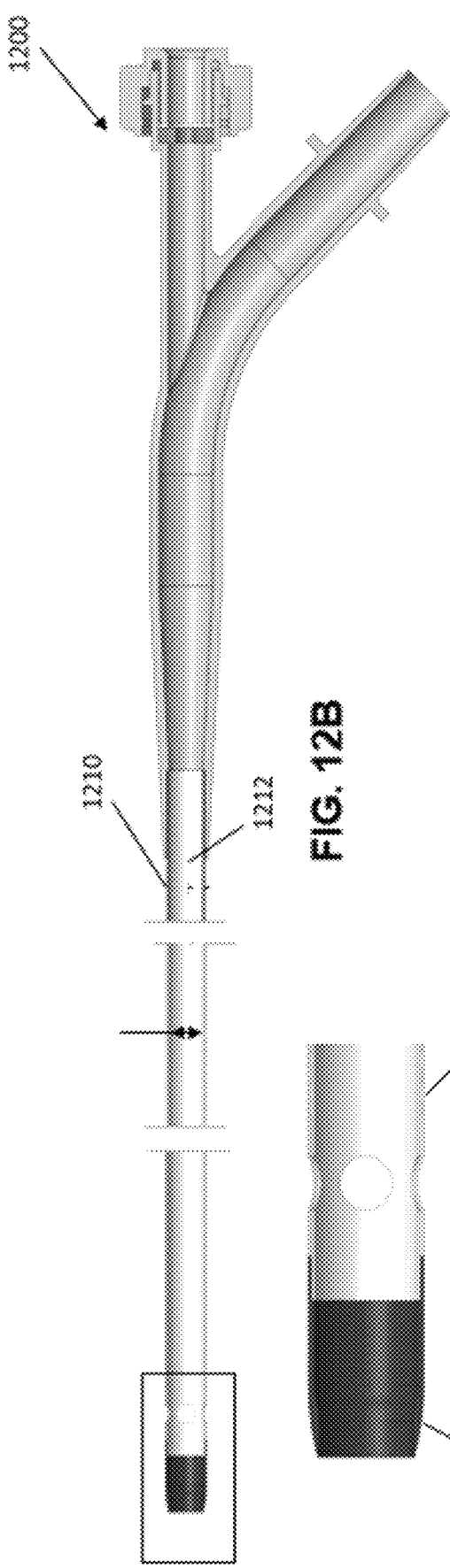
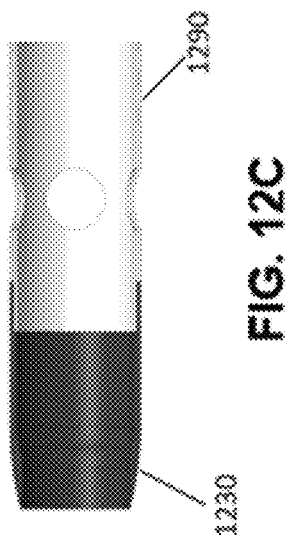
FIG. 12A
FIG. 12B
FIG. 12C

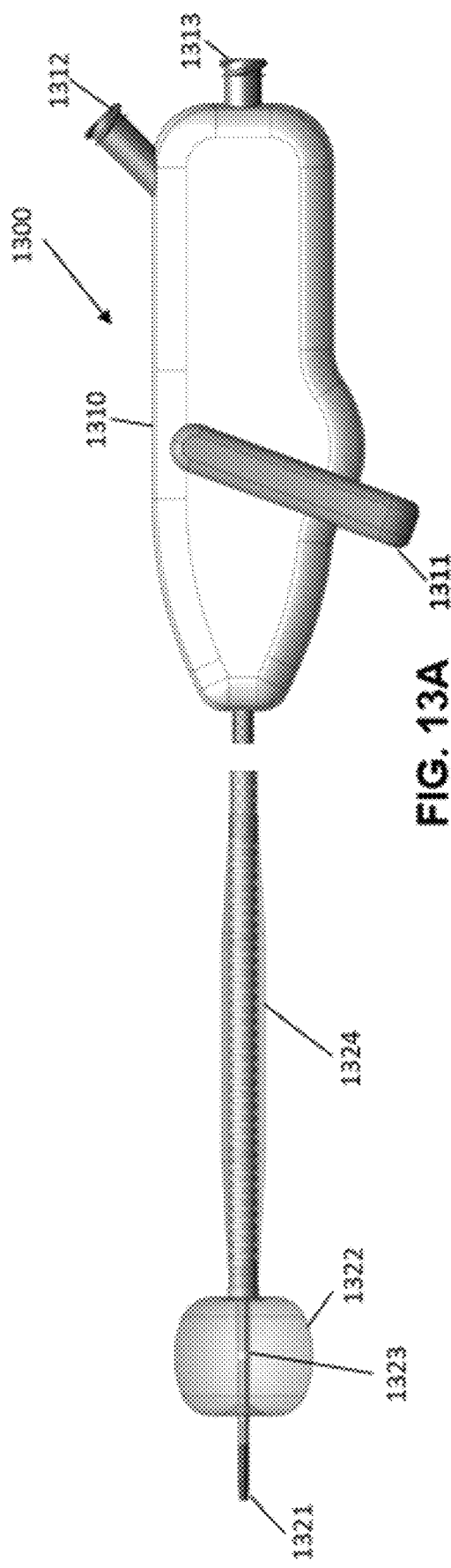
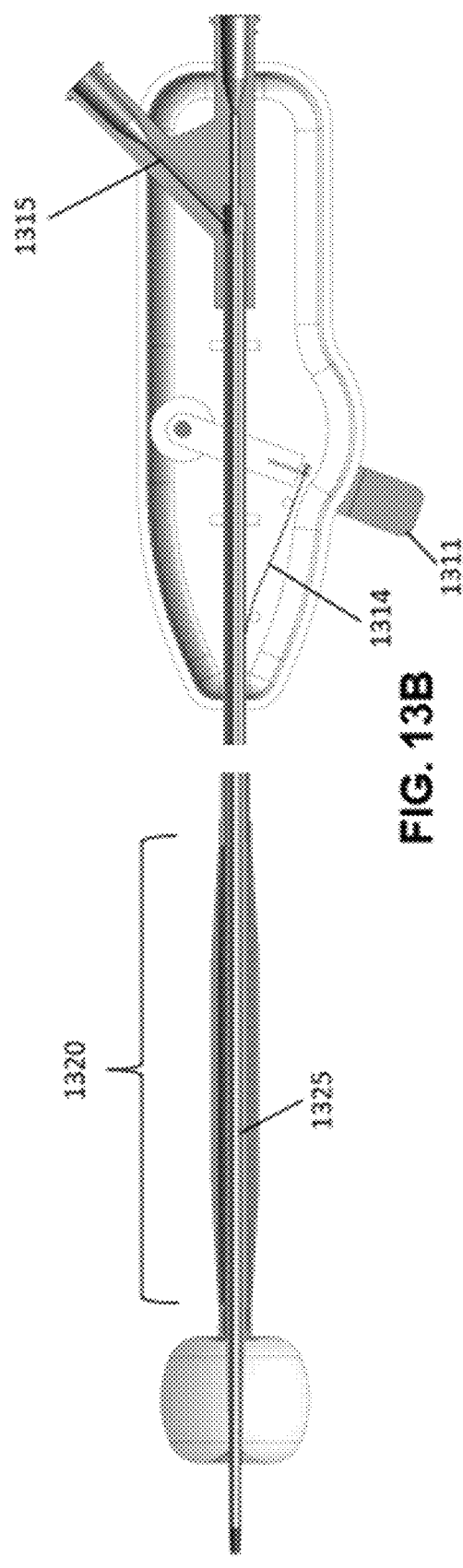
FIG. 13A
FIG. 13B

METHOD AND APPARATUS FOR CATHETER-BASED EXTRACORPOREAL MEMBRANE OXYGENATION (ECMO)

CLAIM OF PRIORITY

None.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein may be related to extracorporeal membrane oxygenation (ECMO). More specifically, the methods and apparatuses described herein may relate to apparatuses that may enable a surgeon to perform ECMO procedures through a catheter guided to a patient's heart region.

BACKGROUND

Historically, heart lung bypass techniques have been used as a core technology for performing open heart surgeries such as coronary bypass grafting, or complex valve replacement or repair. These procedures are typically done in the operating room with an open chest and cannulas inserted into the heart structures, such as the right atrium, and aorta.

Percutaneous, extracorporeal membrane oxygenation (ECMO) using catheter-based systems have been used for short-term ECMO for critically ill patients with cardiopulmonary disease. Conventionally, a large bore sheath or cannula that is placed in the femoral vein, which can be advanced into the iliac vein or possibly the inferior vena cava to allow a high flow removal of deoxygenated venous blood. The blood is then pumped to an extracorporeal membrane oxygenator that oxygenates the blood. A second large bore cannula is placed in the femoral artery, and this is attached to the outflow from the membrane oxygenator and pump to perfuse this oxygenated blood into the iliac artery or distal abdominal aorta. This type of system is commonly referred to as "VA (venous-arterial) ECMO".

Conventional ECMO has been associated with complications that lead to critical limb ischemia secondary to large bore arterial cannula/catheters. These complications can occur in up to ten percent of conventional ECMO procedures and is associated with a higher mortality. Thus, there is a critical need for an improved technology to better enable catheter-based cardiopulmonary bypass/ECMO.

SUMMARY OF THE DISCLOSURE

Described herein are apparatuses, systems, and methods to provide ECMO therapies to a patient. The therapies may be delivered through one or more catheters that are percutaneously delivered and are advanced to the heart region. In some examples, at least one catheter may be advanced through a transseptal puncture, advanced through the left atrium, left ventricle, and into the aorta. Blood may be removed through a venous catheter positioned in the inferior vena cava and returned through an arterial catheter in the aorta.

Any of the methods described herein may be used for transseptal extracorporeal membrane oxygenation. The method may include advancing a first inner catheter that is distally tapered and a second inner catheter through a transseptal puncture, wherein the second inner catheter is coaxial with and surrounds the first inner catheter and an outer surface of the second inner catheter is flush with an outer surface of the first inner catheter, deflecting the first inner catheter within the left atrium so that a distal tip of the first inner catheter is disposed substantially toward an approximate center of a mitral valve, advancing the first inner catheter and the second inner catheter through the approximate center of the mitral valve, deflecting the distal tip of the first inner catheter toward a valve, advancing the first inner catheter and the second inner catheter through the valve, withdrawing the first inner catheter, and receiving, from the patient, oxygen-poor blood through an outer catheter and returning oxygenated blood through the second inner catheter, wherein the outer catheter surrounds the second inner catheter.

Any of the methods described herein may further comprise inflating a balloon disposed around a distal end of the first inner catheter to center the first inner catheter with respect to the mitral valve. In general, the balloon may be inflated with a gas or a liquid, such as saline. Any of the methods described herein can also include inflating the balloon before advancing the first inner catheter and the second inner catheter through the mitral valve.

Any of the methods described herein, deflecting the distal tip of the first inner catheter toward a valve may include deflecting the distal tip by more than 170 degrees with respect to a proximal section of the first inner catheter. In general, the distal tip may be deflected by any feasible amount more than about 140 degrees or more (e.g., 150 degrees or more, 160 degrees or more, 170 degrees or more, etc.).

In any of the methods described herein, the second inner catheter may include a plurality of holes disposed around a body of the second inner catheter to return the oxygenated blood.

In any of the methods described herein, the outer catheter may include a plurality of holes disposed around a body of the outer catheter to receive the oxygen-poor blood (venous blood) and/or blood from the left atrium.

Any of the methods described herein can further include inserting a first guidewire through the first inner catheter, the second inner catheter, and the outer catheter prior to deflecting the first inner catheter within the left atrium. Furthermore, the method can include withdrawing the first guidewire prior to deflecting the distal tip of the first inner catheter toward the valve, and inserting a second guidewire stiffer than the first guidewire, after withdrawing the first guidewire.

Any of the methods described herein can include puncturing the septum between the right atrium and the left atrium before advancing the first inner catheter and the second inner catheter through the transseptal puncture.

Example methods for transseptal extracorporeal membrane oxygenation can include advancing a first catheter that includes an inner sheath and an outer sheath through a transseptal puncture, wherein the outer sheath is coaxial with and surrounds the inner sheath and an outer surface of the outer sheath is flush with an outer surface of the inner sheath, advancing a second catheter into an inferior vena cava, deflecting the inner sheath within the left atrium so that a distal tip of the inner sheath is disposed substantially toward an approximate center of a mitral valve, advancing the inner sheath through the approximate center of the mitral valve, deflecting the distal tip of the inner sheath toward a valve, advancing the first catheter through the valve, withdrawing the inner sheath from the first catheter, and receiving, from the patient, oxygen-poor blood through the second catheter and returning oxygenated blood through the first catheter.

In any of the methods described herein can further include inflating a balloon disposed around a distal end of the inner sheath to center the first inner catheter with respect to the mitral valve. Furthermore, the methods may include inflating the balloon before advancing the inner sheath and the outer sheath through the mitral valve.

In any of the methods described herein, deflecting the distal tip of the inner sheath toward a valve may comprise deflecting the distal tip by more than about 140 degrees (e.g., about 150 degrees or more, about 160 degrees or more, about 170 degrees or more, etc.) with respect to a proximal section of the inner sheath.

In any of the methods described herein, the second catheter can include a plurality of holes disposed around a body of the second catheter to return the oxygenated blood. In a similar manner, in any of the methods described herein, the outer sheath can include a plurality of holes disposed around a body of the outer sheath to receive the oxygen-poor blood.

Any of the methods described herein can further include inserting a first guidewire through the inner sheath and the outer sheath prior to deflecting the inner sheath within the left atrium. Furthermore, any of the methods can further include withdrawing the first guidewire prior to deflecting the distal tip of the inner sheath toward the valve, and inserting a second guidewire stiffer than the first guidewire, after withdrawing the first guidewire.

Any of the methods described herein can include puncturing the septum between the right atrium and the left atrium before advancing the inner sheath and the outer sheath through the transseptal puncture.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 12A shows a region of a catheter-based ECMO system of FIG. 1.

FIG. 12B shows a cross-sectional view of the region of FIG. 12A.

FIG. 12C shows a cross-sectional detailed view of a tip shown in FIG. 12B.

FIG. 13A shows a partial diagram of the catheter-based ECMO system of FIG. 1.

FIG. 13B shows a cross-sectional view of the catheter-based ECMO system of FIG. 1.

DETAILED DESCRIPTION

The present disclosure is related to systems, methods, and apparatuses that solve technical problems related to providing extracorporeal membrane oxygenation (ECMO) therapy through catheter-based systems. Two different systems are described herein. A first system and method uses three distinct catheters. That is, the first system can include a first catheter (sometimes referred to as a sheath), surrounding a second catheter, further surrounding a third catheter. In some examples, the catheters can slide independently within each other. A pull wire attached to a handle can enable the surgeon to deflect a distal tip of the system to guide the insertion and placement of the system. The three catheters can provide the removal of blood from a first location and the return of blood to a second location. A second system can include two separate (non-coupled) catheters. A first catheter may be used to remove blood while a second catheter can be used to return blood.

In general for any system, a catheter is advanced across the atrial septum, through the mitral valve, and into the aorta. This catheter is used to deliver oxygenated blood to the patient. Another catheter, which may be coaxial to other catheters, or may be separate from other catheters, can remove oxygen poor blood from the patient. In some examples, this catheter may be positioned in the inferior vena cava.

Figure 1:
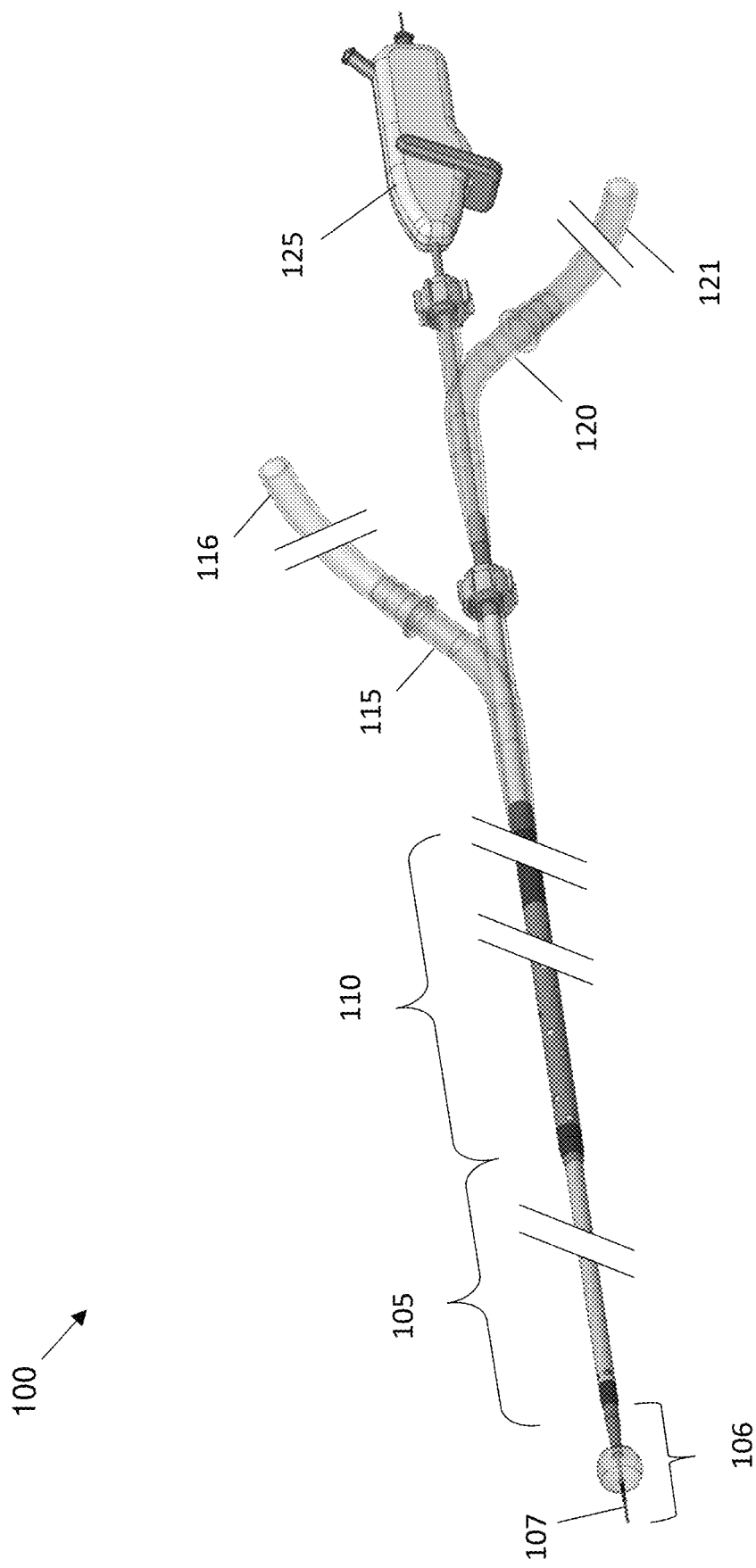
FIG. 1 is an example catheter-based ECMO system.

FIG. 1 is an example catheter-based ECMO system 100. Although described herein, the catheter-based ECMO system 100 may be implemented as an apparatus and be incorporated or included within any other feasible system. In general, the catheter-based ECMO system can include three catheters which are coaxial, concentric and surround each other. For example, the catheter-based ECMO system 100 may include an arterial sheath 105, an arterial sheath inner catheter 106, a guidewire 107, a venous sheath 110, a venous hub 115, an arterial hub 120, and a handle 125. The arterial sheath inner catheter 106 can be a first inner catheter, the arterial sheath 105 can be a second inner catheter, and the venous sheath 110 can be an outer catheter. Notably, as used herein, the terms sheath and catheter may be used interchangeably. Thus, the venous sheath 110 may also be described as a catheter, a sheath, or venous catheter. In other examples, the catheter-based ECMO system 100 may include fewer, more, or different elements.

The catheter-based ECMO system 100 can be used to receive oxygen-poor blood (deoxygenated blood) or blood from the left atrium from a patient, oxygenate the blood outside the patient's body, and return the oxygenated blood to the patient. In general, the catheter-based ECMO system 100 can include three coaxial catheters that are configured to be guided into various veins and arteries of a patient and then provide a means for removing the oxygen-poor blood from the patient, passing the blood through an external oxygenator, and then returning the now oxygenated to the patient. As described herein, the catheter-based ECMO system 100 is advanced through a vein and a distal tip of one of the catheters is further advanced through a transseptal puncture. Blood is removed via another one of the catheters proximal to the distal tip. Oxygenated blood is returned to the patient through the distal tip into the aorta. Operation of the catheter-based ECMO system 100 is described in more detail in conjunction with FIGS. 15A-15I and FIG. 18.

As noted above, the catheter-based ECMO system 100 can include three coaxial catheters: the arterial sheath inner catheter 106, the arterial sheath 105, and the venous sheath 110. The arterial sheath inner catheter 106 may be the inner most catheter (a first inner catheter), surrounded by the arterial sheath 105 (a second inner catheter), further surrounded by the venous sheath 110 (an outer catheter). Blood is removed from the patient via the venous sheath 110 and returned to the patient via the arterial sheath 105. The venous hub 115 is coupled to the venous sheath 110 and allows blood to be transported from the catheter-based ECMO system 100 through tubing 116. Blood from the venous hub 115 is directed to an external oxygenator (not shown).

The arterial hub 120 is coupled to the arterial sheath 105 through one or more lumens. Tubing 121 may be coupled to the arterial hub 120 and the external oxygenator. Oxygenated blood is returned to the patient via the arterial hub 120 and the arterial sheath 105.

The handle 125 may be used to advance and retract the catheter-based ECMO system 100 to and from the patient. In some examples, the handle 125 may be used to deflect a distal end of the arterial sheath inner catheter 106.

One or more guidewires may be included as part of the system. In some examples, the guidewire 107 may be approximately 0.035 inches in diameter. In some other examples, the guidewire 107 may be any greater diameter, such as diameters greater than 0.035 inches (including, but not limited to 0.040, 0.045, 0.050, or any other feasible greater diameter). In some other examples, the guidewire 107 may be any other lesser diameter, including diameters less than 0.035 inches (including, but not limited to 0.030, 0.025, 0.020, or any other feasible smaller diameter). The guidewire 107 may be formed from any feasible material, including Nitinol.

Figure 2A:
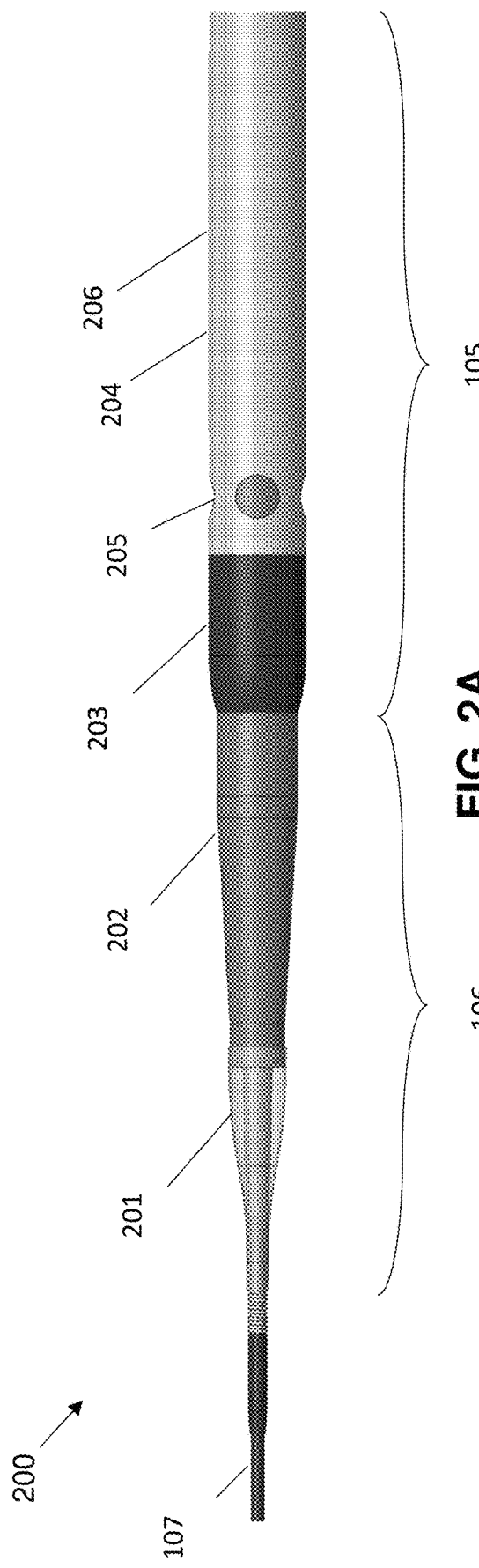
FIG. 2A shows a distal end of a catheter-based ECMO system.

FIG. 2A shows a distal end of a catheter-based ECMO system 200. In some examples, the catheter-based ECMO system 200 may be an example of the catheter-based ECMO system 100 of FIG. 1. Thus, the catheter-based ECMO system 200 can include the guidewire 107, the arterial sheath inner catheter 106, and the arterial sheath 105. The arterial sheath inner catheter 106 may be flexible and can taper from the arterial sheath 105 to the distal tip of the arterial sheath inner catheter 106. The arterial sheath inner catheter 106 may include a balloon 201 and a tapered element 202.

The balloon 201, shown deflated here, may be used during positioning of the catheter-based ECMO system 200. Operation of the balloon 201 is described in more detail below in conjunction with FIGS. 2A, 2B, FIGS. 15A-15I, and FIGS. 17A-17I. The tapered element 202 enables smooth insertion into the patient. The tapered element 202 may be formed from any durable, and generally pliable material. Generally, the tapered element 202 may taper from a larger diameter proximally to a smaller diameter distally.

The arterial sheath 105 can include a tip 203 and an arterial body 204. The arterial body 204 can include one or more infusion holes 205 disposed on the arterial body 204. The arterial body 204 may be covered with a polymer body 206. In general, the arterial sheath 105 is used to return oxygenated blood to the patient. The oxygenated blood may be pumped through the arterial sheath 105 through the infusion holes 205. In some examples, the arterial sheath inner catheter 106 may be withdrawn from the arterial sheath 105 allowing oxygenated blood to be returned through an opening of the tip 203.

Figure 2B:
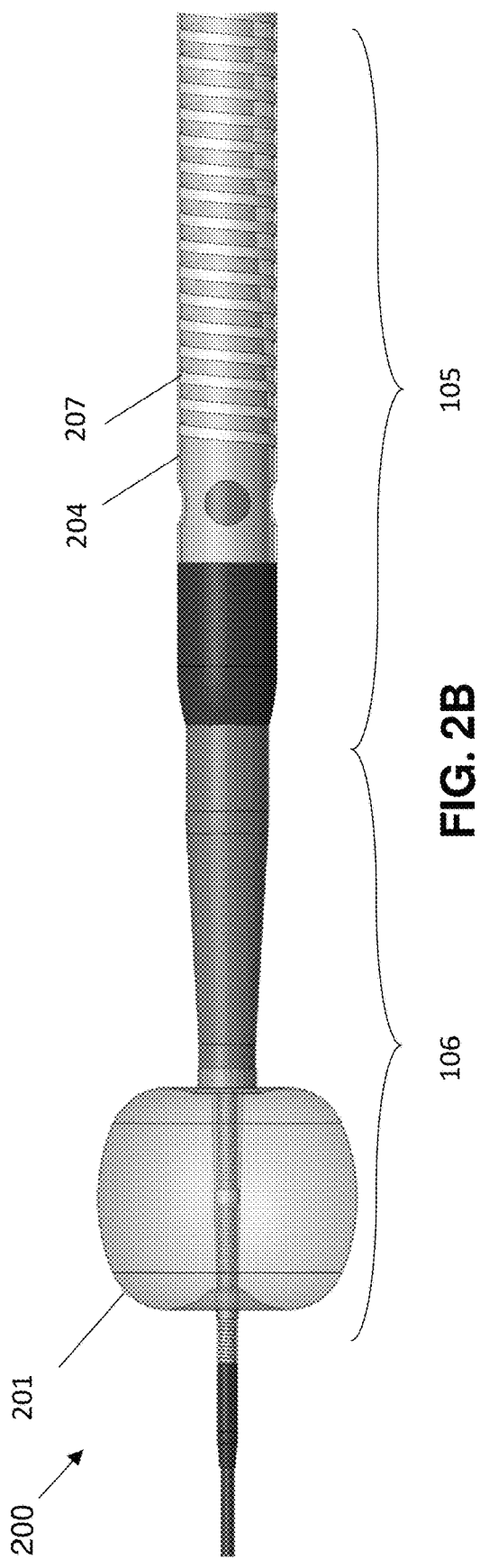
FIG. 2B shows another view of the distal end of the catheter-based ECMO system.

FIG. 2B shows another view of the distal end of the catheter-based ECMO system 200. In this view, the arterial sheath 105 is depicted with an inner hypotube 207. In general, the hypotube 207 may be disposed underneath the polymer body 206. The hypotube 207 may provide flexible rigidity for the arterial sheath 105. That is, the hypotube 207 can be more rigid toward the handle (not shown) and more flexible toward the tip 203.

The balloon 201 is shown inflated. The balloon 201 may help guide or center the arterial sheath inner catheter 106 during insertion into the patient, particularly within the patient's heart, and may assist in the safe crossing of the mitral valve.

Figure 3:
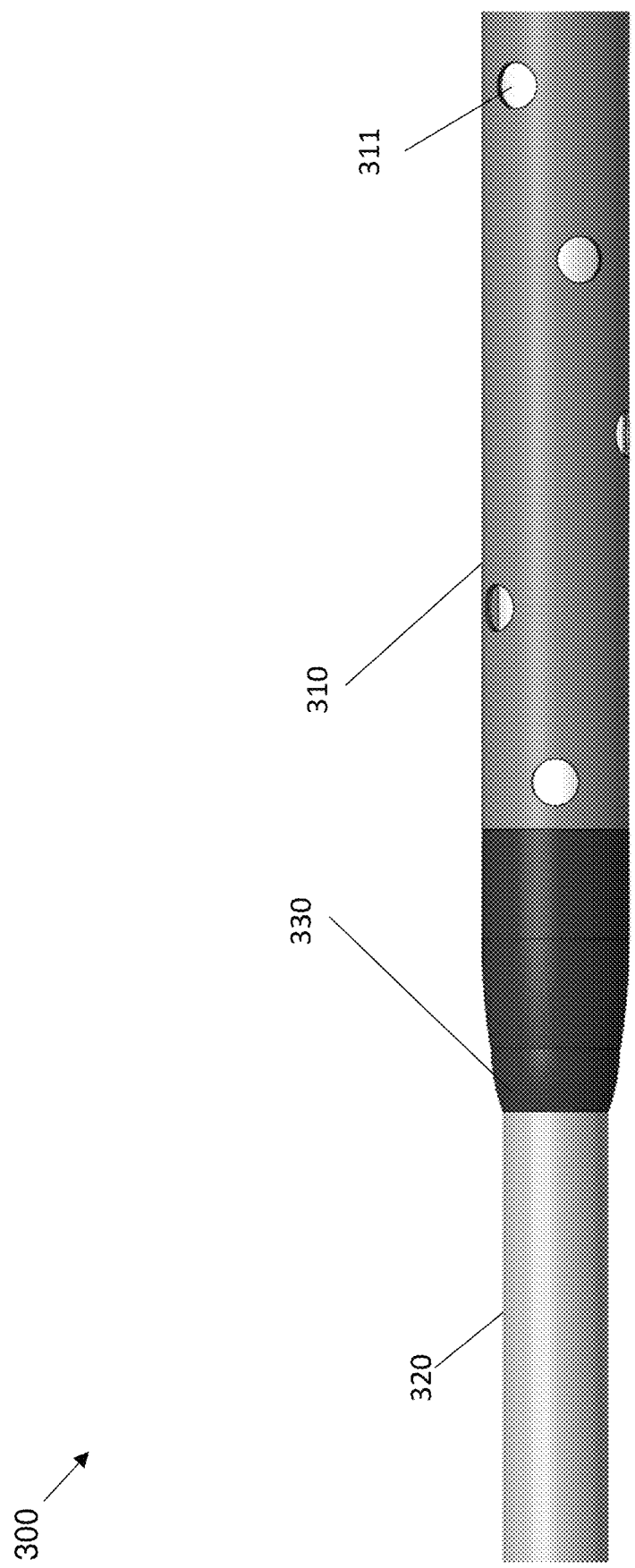
FIG. 3 shows another view of a catheter-based ECMO system.

FIG. 3 shows another view of a catheter-based ECMO system 300. In some examples, the catheter-based ECMO system 300 may be an example of the catheter-based ECMO system 100 of FIG. 1. In particular, FIG. 3 shows a transition between a venous sheath 310 (another example of the venous sheath 110) and an arterial sheath 320 (which can be another example of the arterial sheath 105).

In some examples the venous sheath 310 may have a size of approximately 30 Fr and arterial sheath 320 may have a size of approximately 22 Fr. In general, the size of the arterial sheath 320 may be smaller than the size of the venous sheath 310 to allow the arterial sheath 320 to be fully coaxial with respect to the venous sheath 310. The venous sheath 310 may include a plurality of inflow holes 311 disposed about the sides of the venous sheath 310.

The catheter-based ECMO system 300 may include a compliant and durable seal 330 between the venous sheath 310 and the arterial sheath 320. The seal 330 may be made of any feasible and generally lubricious material that can provide a liquid-tight (watertight) seal to the arterial sheath 320. In some examples, there may be a slight interference fit between an inner diameter of the seal 330 and an outer diameter of the arterial sheath 320.

Figure 4:
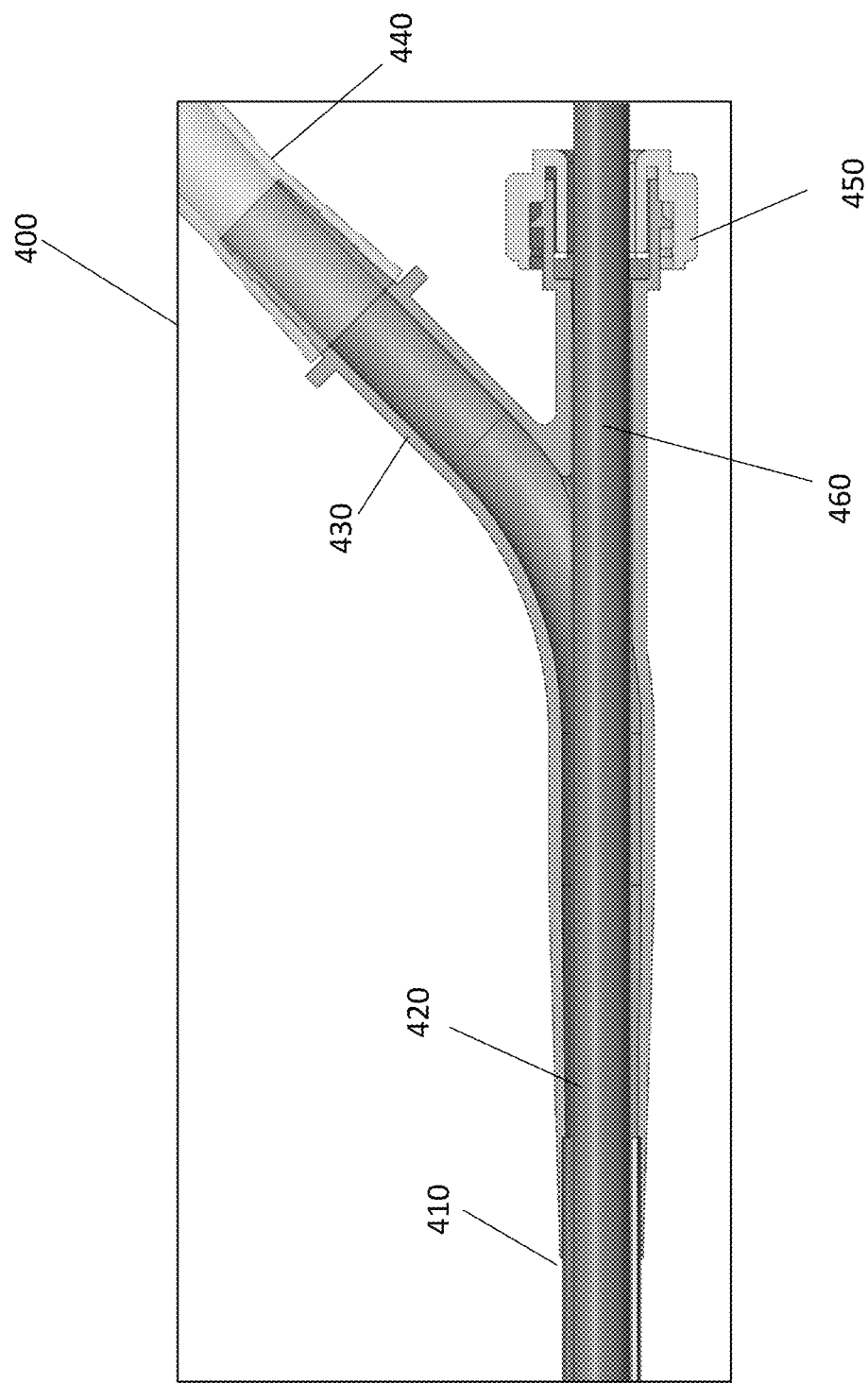
FIG. 4 shows an example venous hub.

FIG. 4 shows an example venous hub 400. The venous hub 400 may be an example of the venous hub 115 of FIG. 1. The venous hub 400 includes a venous sheath 410, a venous lumen 420, a venous port 430, an arterial shaft 460, and a hemostasis valve 450.

The venous sheath 410 can extend distally from the venous hub 400 and can be an example of the venous sheath 110. Notably, the venous lumen 420 can be coupled to the venous sheath 410 and allow oxygen-poor blood to flow from the patient through the venous port 430 further through optional tubing 440. Typically, the tubing 440 can direct the blood toward an oxygenator. In some examples, the tubing 440 is ⅜ inches in an inner or outer diameter. However, in other examples, the tubing 440 can be any feasible inner or outer diameter.

The hemostasis valve 450 may allow other lumens or shafts to pass through the venous hub 400. As shown, the hemostasis valve 450 may allow an arterial shaft 460 to pass therethrough.

Figure 5:
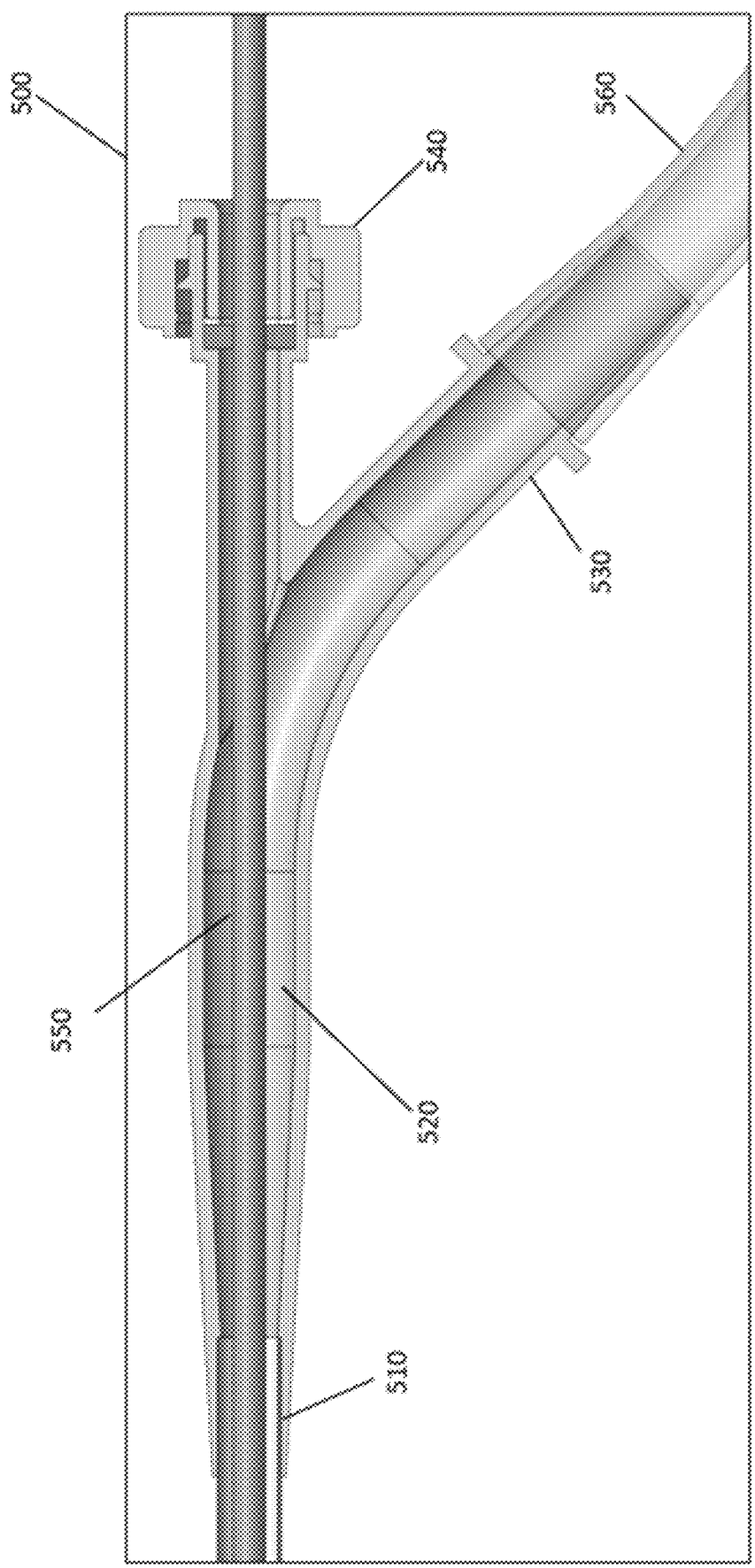
FIG. 5 shows an example arterial hub.

FIG. 5 shows an example arterial hub 500. The arterial hub 500 may be an example of the arterial hub 120 of FIG. 1. The arterial hub 500 may include an arterial sheath 510, an arterial lumen 520, an arterial port 530, and a hemostasis valve 540.

The arterial sheath 510 can extend distally from the arterial hub 500 toward a proximal end of the venous hub 400 of FIG. 4. The arterial lumen 520 can be coupled to the arterial sheath 510 can allow oxygenated blood to flow from an external oxygenator to the patient. The oxygenated blood may be received through optional tubing 560. The arterial hub 500 can include the hemostasis valve 540 that is liquid tight and allows an inner catheter shaft 550 to enter and pass through the arterial hub 500 Similar to the hemostasis valve 450, the hemostasis valve 540 can be liquid tight.

Figure 6:
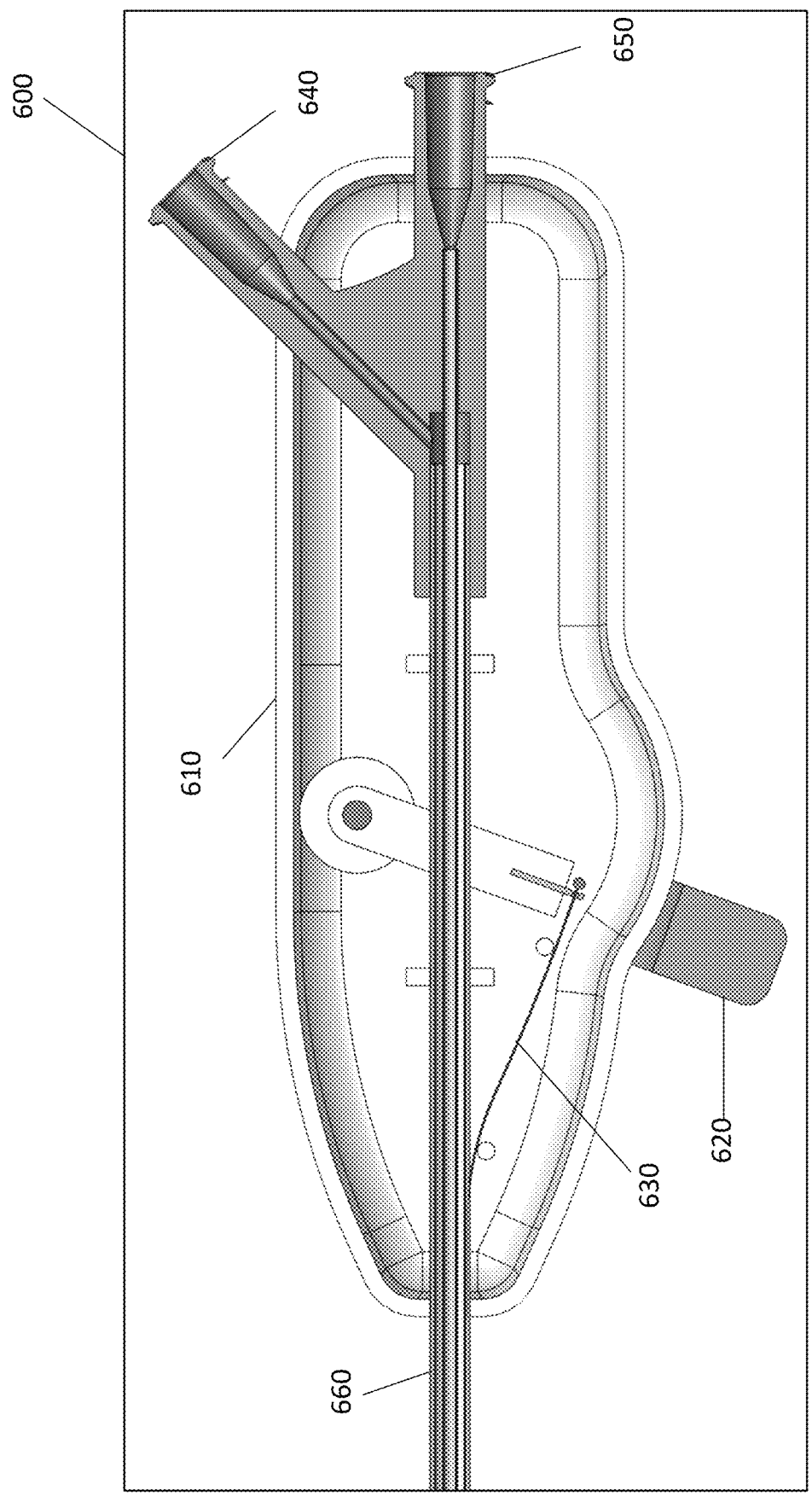
FIG. 6 shows a cutaway view of a handle.

FIG. 6 shows a cutaway view of a handle 600. The handle 600, can be another example of the handle 125 of FIG. 1. The handle 600 may include a body 610, a lever 620, a pull wire 630, a balloon inflation port 640, and a guidewire port 650. The handle 600 may be coupled to an arterial sheath inner catheter 660 which may be an example of the arterial sheath inner catheter 106.

The body 610 may function as a housing to contain any of the elements described herein. In particular, the body 610 may support, mount, and/or house the lever 620, the balloon inflation port 640, and the guidewire port 650. The lever 620 is coupled to the pull wire 630. Together, the lever 620 and the pull wire 630 and be used to deflect a distal end of the arterial sheath inner catheter 660. The balloon inflation port 640 (sometimes referred to as a luer port) may receive a gas or liquid (saline, CO2, or the like) to inflate a balloon distally located with respect to the handle 600. In a similar manner, the guidewire port 650 may receive a guidewire. The guidewire may be an example of the guidewire 107.

Figure 7A:
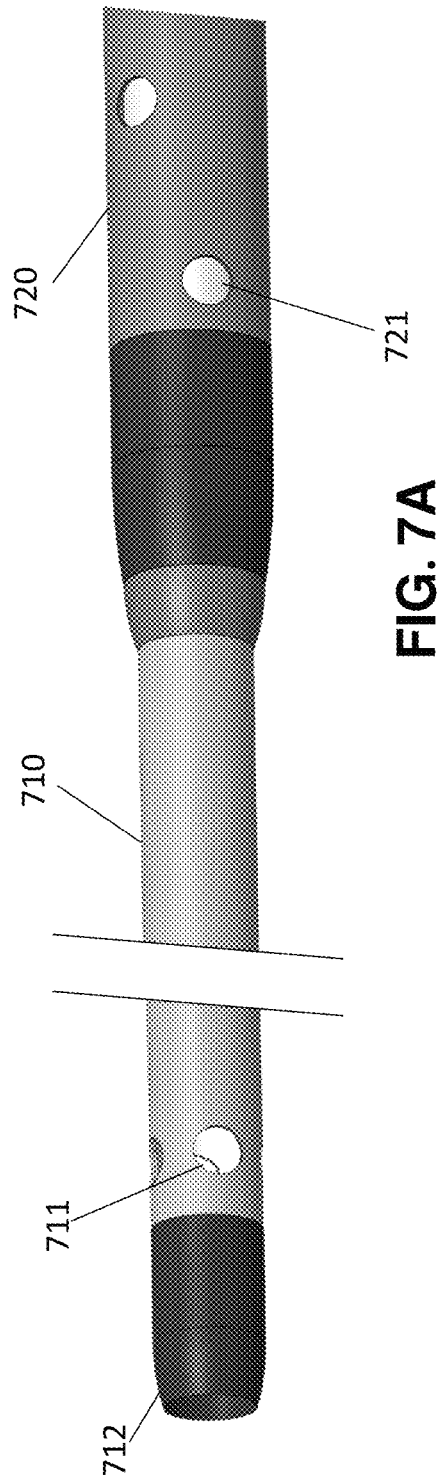
FIGS. 7A and 7B show a distal end of the catheter-based ECMO system of FIG. 1.
Figure 7B:
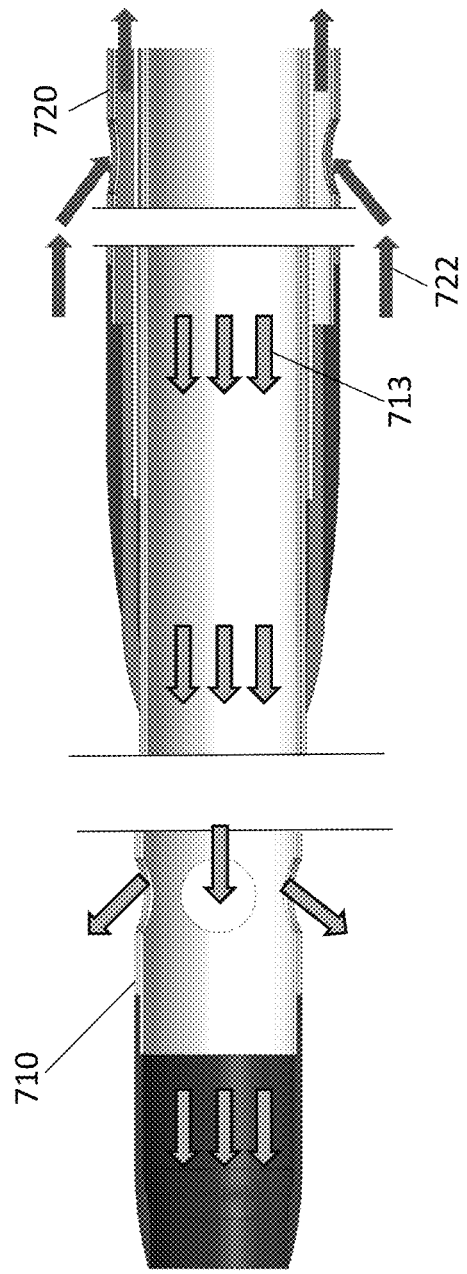

FIGS. 7A and 7B show a distal end of the catheter-based ECMO system 100 of FIG. 1. Both FIGS. 7A and 7B show the catheter-based ECMO system 100 with the arterial sheath inner catheter removed. FIG. 7A includes an arterial sheath 710 and a venous sheath 720. The arterial sheath 710 can be an example of the arterial sheath 105 and the venous sheath 720 can be an example of the venous sheath 110, both of FIG. 1.

The venous sheath 720 can include a plurality of inflow holes 721 that enable blood to be received to the venous sheath 720. The arterial sheath can include a plurality of infusion holes 711 as well as an infusion opening 712 located on a distal end of the arterial sheath 710. The infusion holes 711 and the infusion opening 712 allow blood to be returned to the patient.

FIG. 7B shows a detailed cross-sectional view of the distal end catheter-based ECMO system 100. For example, the arterial sheath 710 and the venous sheath 720 are shown in cross section. Oxygenated blood may flow out of the arterial sheath 710. Arrows 713 illustrate blood flow from the catheter-based ECMO system 100. Blood may be removed from the patient through the venous sheath 720. Arrows 722 illustrate blood flow from the patient and through the venous sheath 720.

Figure 8:
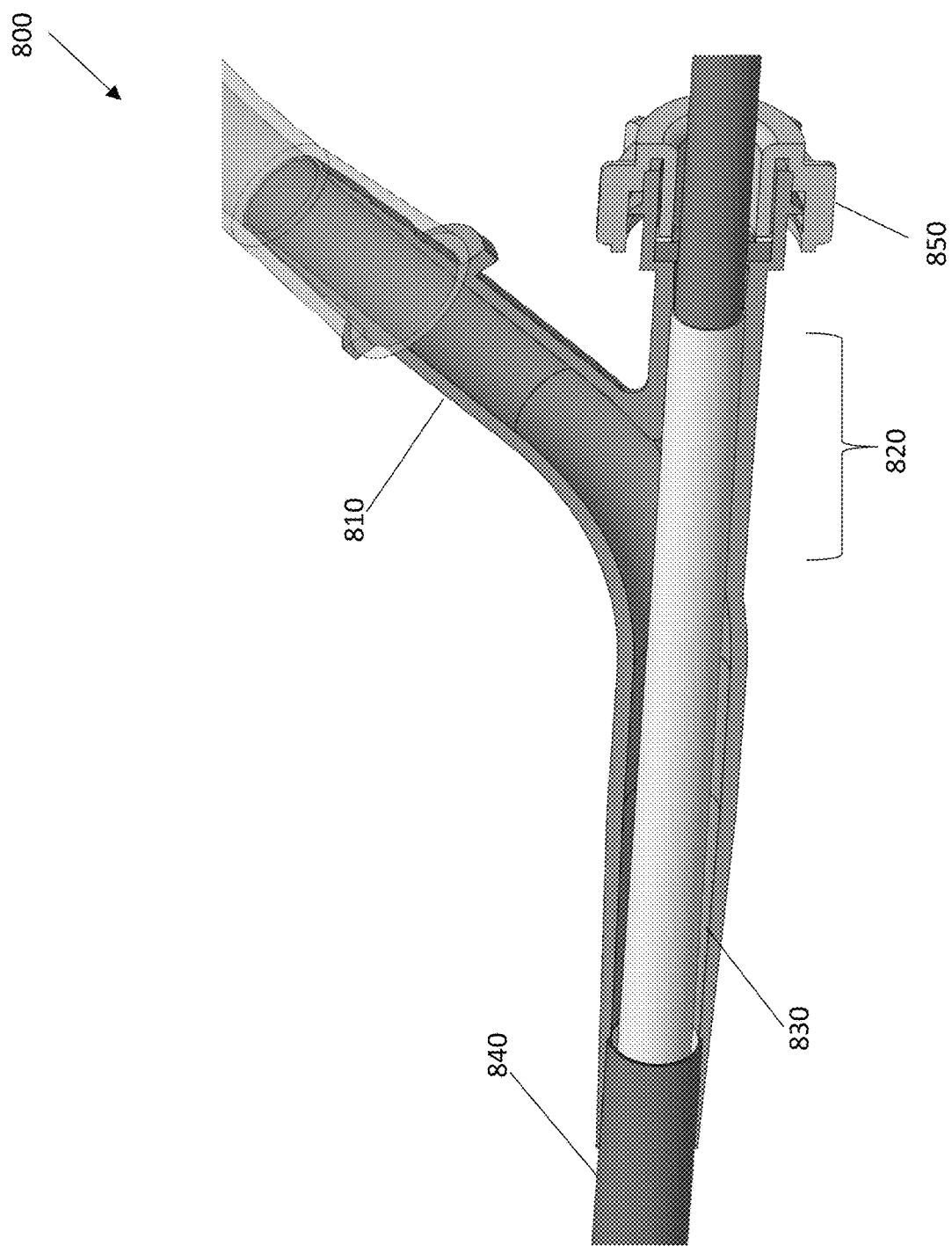
FIG. 8 shows a cross-sectional view of an example venous hub.

FIG. 8 shows a cross-sectional view of an example venous hub 800. The venous hub 800 may be a example of the venous hub 115 of FIG. 1. The venous hub 800 may include a venous port 810, a venous sheath inner liner 820, a venous sheath 840, and a venous sheath lumen 830. In some examples, the venous sheath lumen 830 may be separate or may be integral (combined) with the venous sheath 840. Blood may be received from inflow holes (not shown) on the venous sheath 840, through the venous sheath inner liner 820, transported through the venous port 810 and directed to an oxygenator. An arterial sheath 850 may pass substantially through the venous hub 800 to an arterial hub (not shown).

Figure 9:
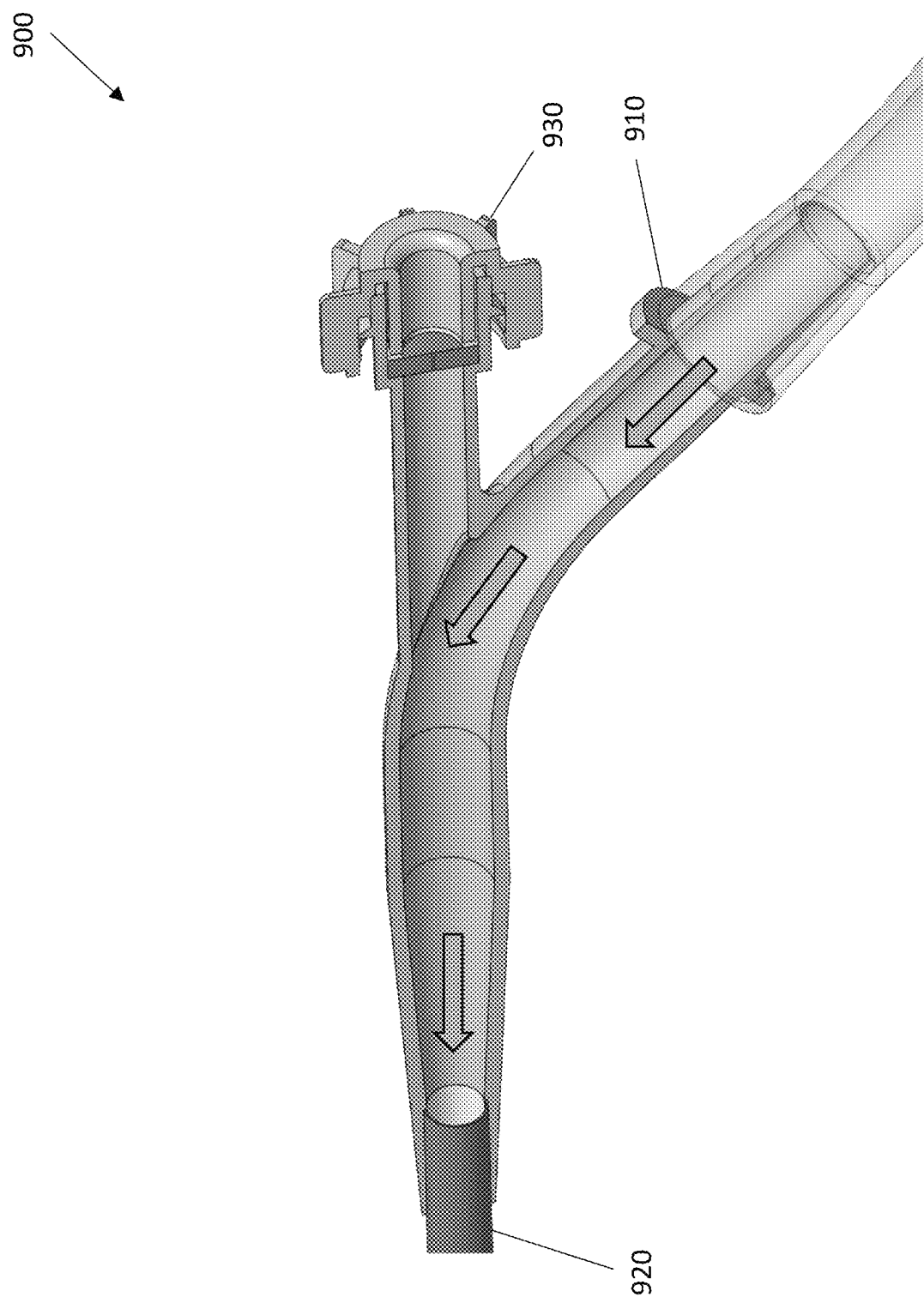
FIG. 9 shows a cross-sectional view of an example arterial hub.

FIG. 9 shows a cross-sectional view of an example arterial hub 900. The arterial hub 900 may be an example of the arterial hub 120 of FIG. 1. The arterial hub 900 may include an arterial port 910, an arterial sheath 920, and a hemostasis valve 930. Oxygenated blood may be received through the arterial port 910 and transported through the arterial sheath 920. In FIG. 9, the arterial sheath inner catheter is not shown (for example, may be removed) from the arterial hub 900. The hemostasis valve 930 is shown closed.

Figure 10A:
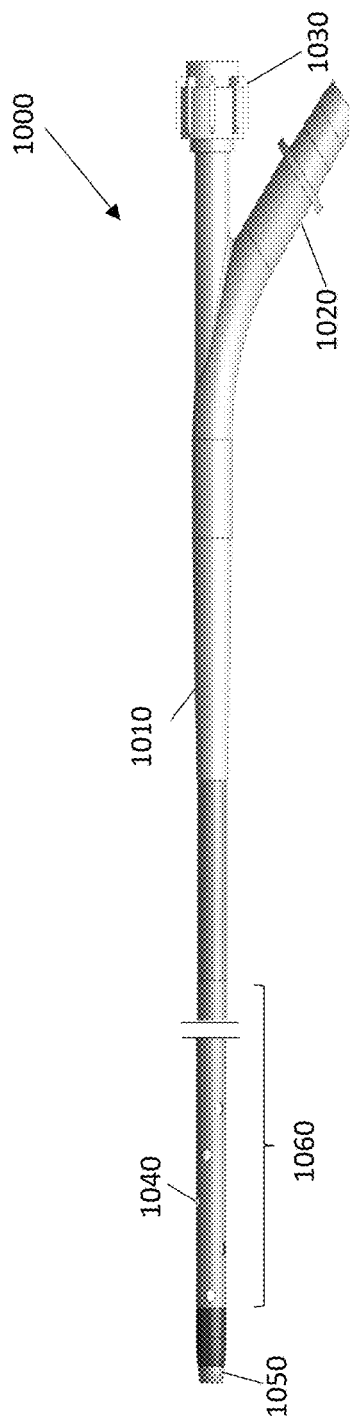
FIG. 10A shows a region of the catheter-based ECMO system 100 of FIG. 1.

FIG. 10A shows a region 1000 of the catheter-based ECMO system 100 of FIG. 1. The region 1000 may include a venous sheath 1010, a venous hub 1020, a hemostasis valve 1030, and a tip 1050. The venous sheath 1010 may include a plurality of inflow holes 1040 to receive blood that may be directed through the venous hub 1020 to an oxygenator.

The tip 1050 may be positioned distally with respect to the venous hub 1020. In some examples, the tip 1050 may be formed from a radiopaque material (such as, but not limited to a tungsten loaded pebax). A region 1060 of the venous sheath 1010 may have a variable stiffness (e.g., have a multi-durometer). For example, the stiffness or flexibility of the venous sheath 1010 may decrease as you move away from the hemostasis valve 1030 toward the tip 1050. The variable stiffness of region 1060 may assist in placement and positioning the catheter-based ECMO system within the patient. In some examples, an outer diameter of the venous sheath 1010 can be approximately 28 Fr.

Figure 10B:
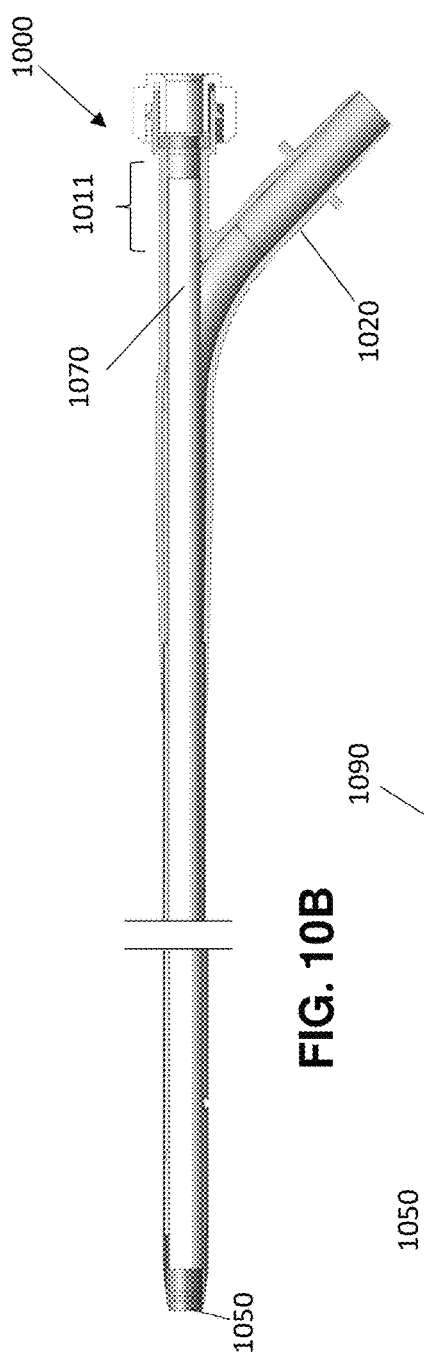
FIG. 10B shows a cross-sectional view of the region shown in FIG. 10A.

FIG. 10B shows a cross-sectional view of the region 1000 of FIG. 10A. The cross-sectional view shows an inner liner 1070 that may be bonded to the venous sheath 1010. An example bonding region is shown as region 1011. The bond in region 1011 may seal blood from leaking at the venous hub 1020. The inner liner 1070 may provide lumen to receive a guidewire. In some examples, an inner diameter of the inner liner 1070 may be approximately 21 Fr.

Figure 10C:
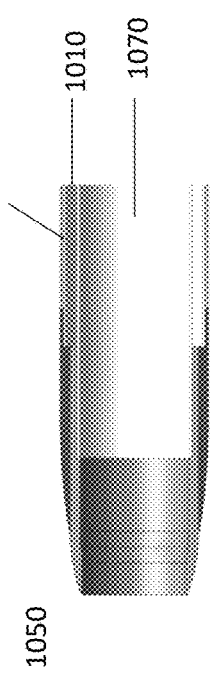
FIG. 10C shows a cross-sectional detailed view of a tip of the region shown in FIG. 10A.

FIG. 10C shows a cross-sectional detailed view of the tip 1050 of the region 1000. In some examples the tip 1050 may be a two-layer tip that may be bonded to an outer jacket 1090 of the venous sheath 1010 and the inner liner 1070. Furthermore, the inner diameter of the distal tip 1050 may be approximately 20 Fr. The outer jacket 1090 and the inner liner 1070 cooperatively form a lumen that can carry blood from the plurality of inflow holes 1040 to the venous hub 1020.

Figure 11A:
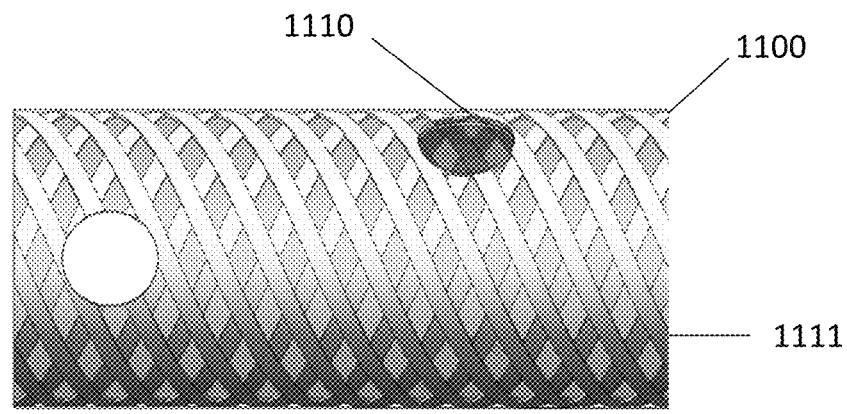
FIG. 11A shows an example braid-reinforced shaft.

FIG. 11A shows an example braid-reinforced shaft 1100. The braid-reinforced shaft 1100 may be included within the arterial sheath 105 or the venous sheath 110 of FIG. 1. As described herein, each of the arterial sheath 105 and the venous sheath 110 can include a plurality of holes 1110 disposed on the sides of the sheaths. In some examples, the holes 1110 may be laser ablated. The braid-reinforced shaft 1100 may include a polymer outer jacket 1111 bonded to a braided material. The braided material can be stainless steel, Nitinol, or any other feasible material.

Figure 11B:
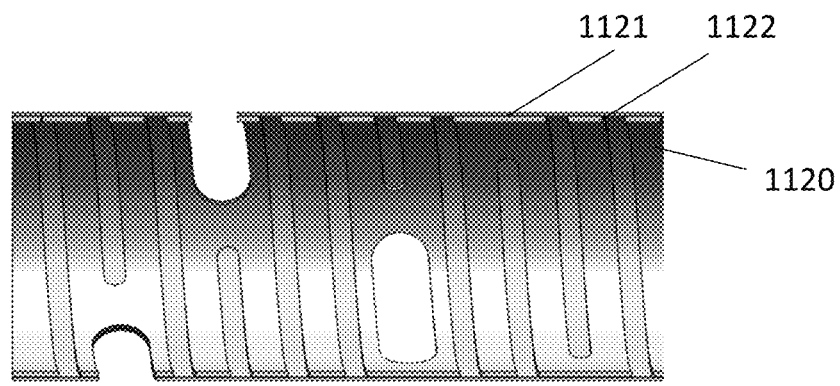
FIG. 11B shows a cross section of another reinforced shaft.
Figure 11C:
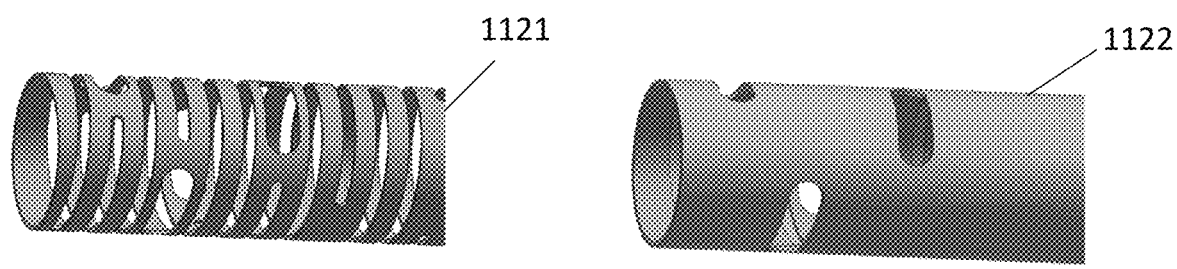
FIG. 11C shows separate views of the hypotube and the polymer jacket.

FIG. 11B shows a cross section of another reinforced shaft 1120. The reinforced shaft 1120 may include a laser cut hypotube 1121 and a polymer jacket 1122. In some examples, the polymer jacket 1122 may be bonded to the hypotube 1121. Furthermore, the reinforced shaft 1120 may be laser ablated such that holes may be formed in the polymer jacket 1122 and the hypotube 1121 simultaneously. FIG. 11C shows separate views of the hypotube 1121 and the polymer jacket 1122.

FIG. 12A shows a region 1200 of a catheter-based ECMO system 100 of FIG. 1. The region 1200 includes an arterial sheath 1210, a tip 1230, a hemostasis valve 1240, and an arterial hub 1250. The arterial sheath 1210 can include a region 1211 that has a variable stiffness. For example, the arterial sheath 1210 can be stiffer closer to the arterial hub 1250 and more flexible (less stiff) farther away from the arterial hub 1250. The varying stiffness may help position the catheter-bases ECMO system 100 within the patient. In some examples, the region 1211 may include a braid-reinforced section closer to the arterial hub 1250 and a coil section further from the arterial hub 1250.

Infusion holes 1220 may be disposed on the side of the arterial sheath 1210. In some examples, the arterial sheath 1210 may include a tip 1230 which may be radiopaque. In some implementations, the tip 1230 may be formed from a tungsten loaded pebax, however, any other feasible material may be used. In some examples, an outer diameter of the arterial sheath 1210 can be approximately 20 Fr.

FIG. 12B shows a cross-sectional view of the region 1200 of the catheter-based ECMO system 100 of FIG. The arterial sheath 1210 may include an inner lumen 1212. In some examples, the inner lumen 1212 can have an inner diameter of approximately 18 Fr. In some examples, the inner lumen 1212 can be coated with a lubricious coating such as, but not limited to, a polytetrafluoroethylene (PTFE).

FIG. 12C shows a cross-sectional detailed view of the tip 1230 of the region 1200. In some examples the tip 1230 may be bonded to an outer jacket 1290 of the venous sheath 1010 and the inner liner. Furthermore, the inner diameter of the distal tip 1050 may be approximately 17 Fr.

FIG. 13A shows a partial diagram 1300 of the catheter-based ECMO system 100 of FIG. 1. In particular, the diagram 1300 may show a portion of an arterial sheath inner catheter that includes a handle 1310 and a distal region 1320. The distal region 1320 may generally be a distal region of an arterial sheath, such as the arterial sheath 105 of FIG. 1. The diagram 1300 may include a tip 1321, a balloon 1322, a marker 1323, and a tapered element 1324.

The tip 1321 may be formed from any feasible material, such as a radiopaque material. In general, the tip 1321 is formed from a soft material. The balloon 1322 may be inflated to help center the arterial sheath inner catheter respect to a mitral value. The use of catheter-based ECMO system 100 in general, and the balloon 1322 in particular is described in more detail below with respect to FIGS. 15A-15I and FIG. 18. A radiopaque marker 1323 may be surrounded by the balloon 1322. In some examples, the marker 1323 may be used to help locate at least the balloon 1322 as the catheter-based ECMO system 100 in the patient. The tapered element 1324 may surround a hypotube.

The handle 1310 may include a lever 1311, balloon inflation port 1312 and a guidewire port 1313. The balloon inflation port 1312 may be coupled with a lumen to the balloon 1322. The balloon 1322 may be inflated with the application of a liquid or gas through the balloon inflation port 1312. The guidewire port 1313 can receive a guidewire (such as the guidewire 107 of FIG. 1) to help guide and position the catheter-based ECMO system 100 within the patient. The lever 1311 may be used to move a pull wire (not shown) to deflect the tip 1321.

FIG. 13B shows a cross-sectional view of the catheter-based ECMO system 100 which can include a lumen 1325, a deflection pull wire 1314, a balloon inflation lumen 1315. The lumen 1325 can be used by the guidewire. One end of the deflection pull wire 1314 is coupled to the lever 1311, while another end of the deflection pull wire 1314 may be coupled to the tip 1321.

Figure 14A:
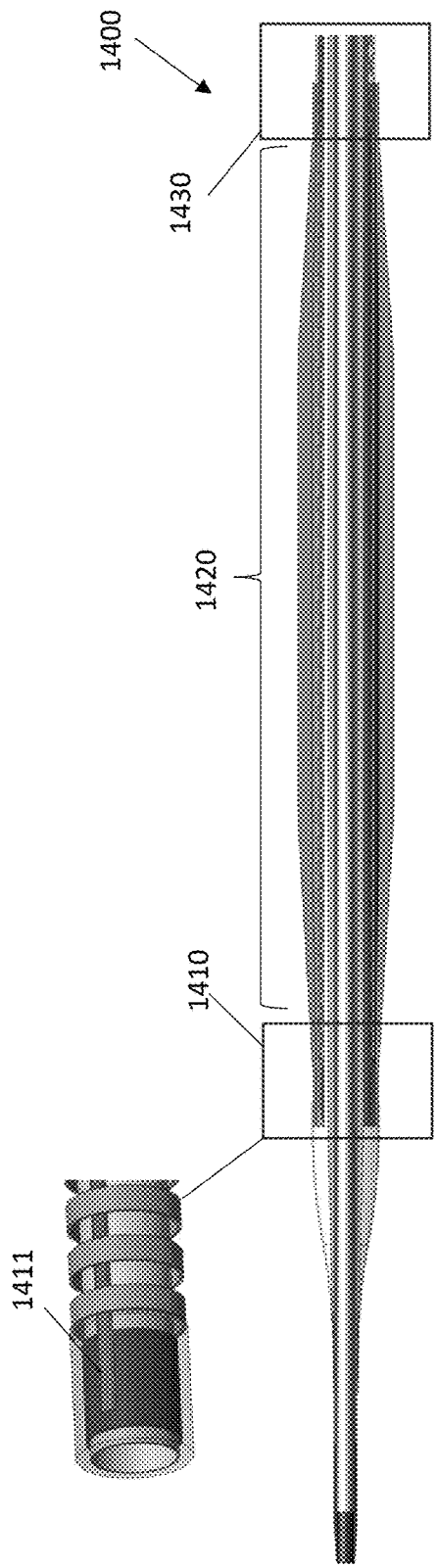
FIG. 14A shows a partial view of an arterial sheath inner catheter.

FIG. 14A shows a partial view of an arterial sheath inner catheter 1400. The arterial sheath inner catheter 1400 can be an example of the arterial sheath inner catheter 106 of FIG. 1. The arterial sheath inner catheter 1400 can include a first fused region 1410, an unfused region 1420, and a second fused region 1430. The first and second fused regions 1410, 1430 can be regions of the arterial sheath inner catheter 1400 where various layers and elements are fused together. In contrast, the unfused region 1420 may include those same or similar elements, but they may not be fused together. The unfused region 1420 may enable the arterial sheath inner catheter 1400 to more easily bend in response to a pull wire, such as pull wire 1411. In some examples, the unfused region 1420 may be between approximately 7-9 centimeters. In other examples, the unfused region 1420 can be any feasible length.

Figure 14B:
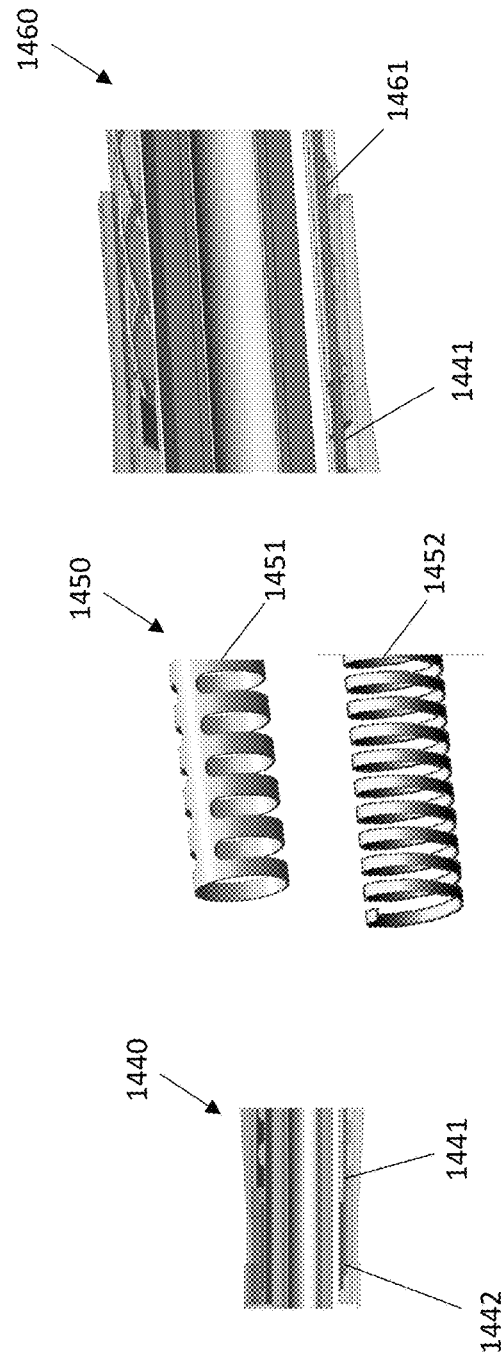
FIG. 14B shows some example elements of the arterial sheath inner catheter.

FIG. 14B shows some elements of the arterial sheath inner catheter 1400. Region 1440 can correspond to the first fused region 1410 and include a pull wire 1441 fused to a distal band 1442. Region 1450 show various hypotube constructions that may be included within the unfused region 1420. Such constructions may enable the arterial sheath inner catheter 1400 to bend in response to a force provided through the pull wire 1441. For example, the hypotube may be a laser cut hypotube 1451 with a spine to control planar deflection. In another example, the hypotube can be a coil hypotube 1452. The coil hypotube 1452 can also be a spring hypotube.

Region 1460 can correspond to the second fused region 1430. The region 1460 shows the pull wire 1441 along with a lubricious lumen 1461 for the pull wire 1441. The lumen 1461 can allow the pull wire 1441 to move freely within the catheter-based ECMO system 100.

FIGS. 15A-15I show example steps of using the catheter-based ECMO system 100 of FIG. 1. The steps described herein are merely exemplary and are not meant to be limiting. Other steps may be used, and in some cases, these steps may be performed in a different order.

Figure 15C:
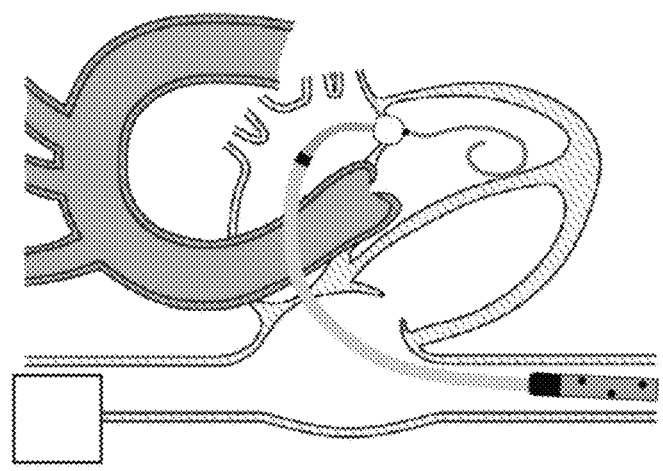
FIGS. 15A-15I show example steps of using the catheter-based ECMO system of FIG. 1.
Figure 15B:
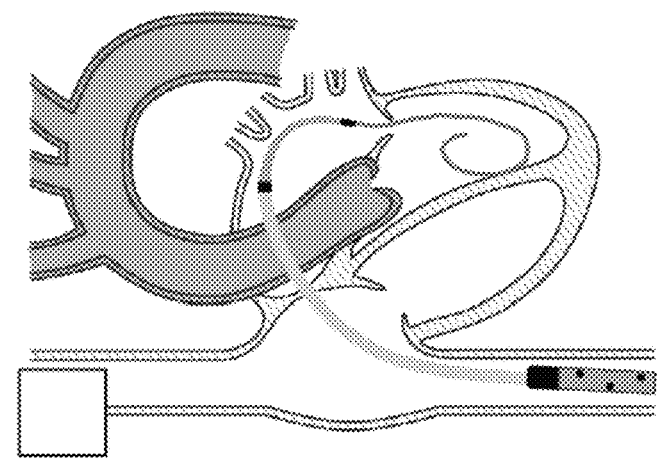
Figure 15A:
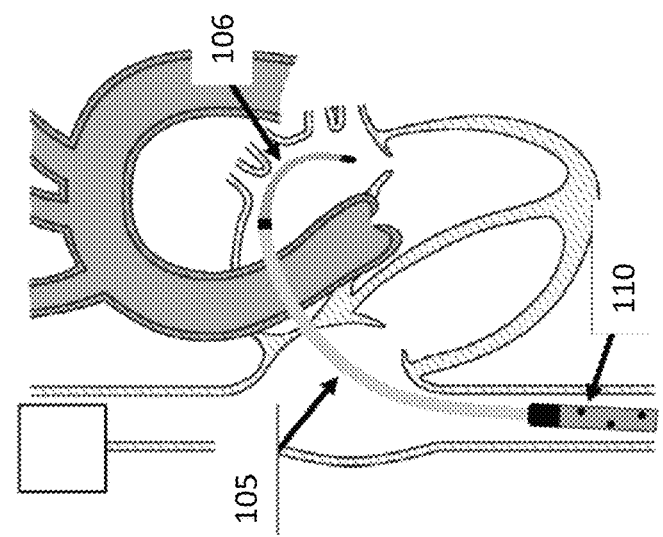

In FIG. 15A, the catheter-based ECMO system 100 is advanced through the atrial septum. In some examples, a 0.035 inch guidewire may be used to help position the catheter-based ECMO system 100. As shown, the venous sheath 110 may be within the inferior vena cava while the arterial sheath 105 and the arterial sheath inner catheter 106 may puncture the septum. The arterial sheath inner catheter 106 may be turned/bent/deflected (through a pull wire, for example) into the left atrium.

Next, in FIG. 15B, the guidewire may be advanced into the left ventricle. For example, the surgeon can carefully guide the guidewire through the mitral valve. In some examples, the guidewire can be a relatively compliant (floppy) guidewire.

Next, in FIG. 15C, the arterial sheath 105 and arterial sheath inner catheter 106 can be advanced toward the mitral valve. In some cases, the surgeon may adjust deflection of the inner catheter to position the balloon (such as balloon 201 of FIG. 2) across the mitral valve. After positioning the balloon, the balloon can be inflated. In some examples, the balloon may be inflated by saline or gas. Inflation of the balloon helps to center the arterial sheath inner catheter with respect to the mitral valve, and prevent the passage of the catheter between the mitral valve chordae tendinae. Note that advancement of the arterial sheath 105 and the arterial sheath inner catheter 106 can be independent of the venous sheath 110. Thus, the venous sheath 110 can remain in the inferior vena cava.

Figure 15F:
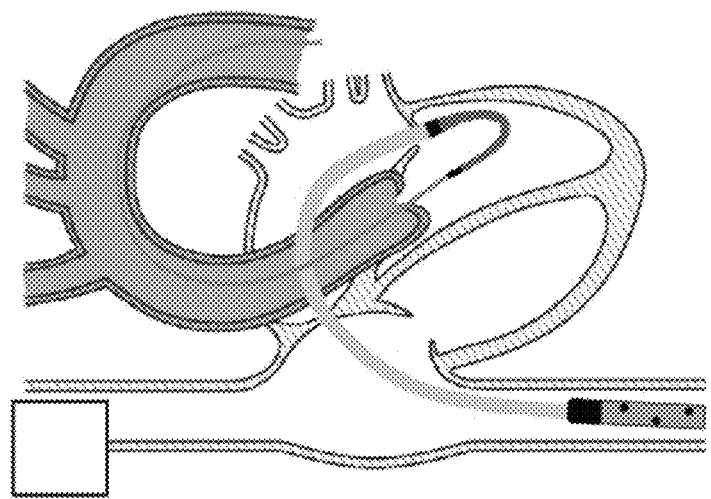
Figure 15E:
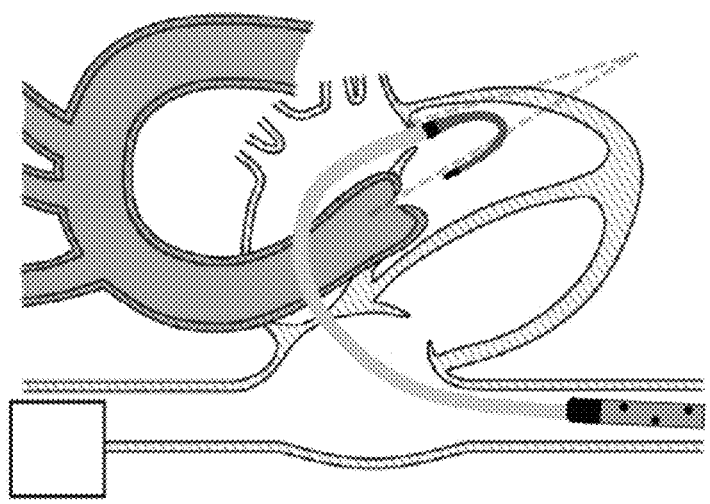
Figure 15D:
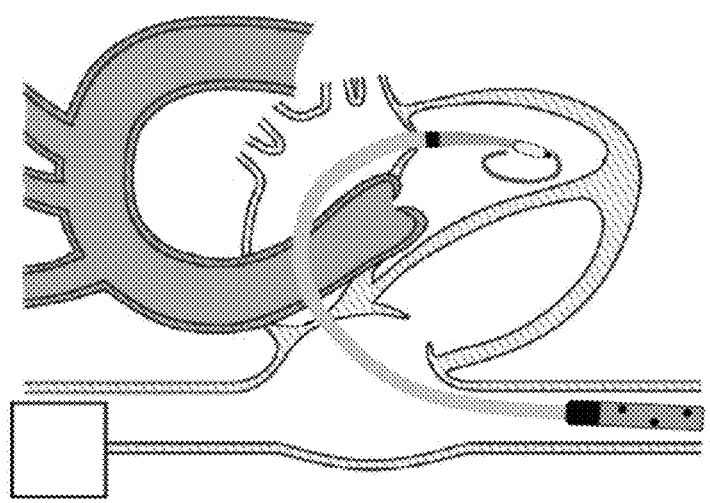

Next, in FIG. 15D after crossing through the mitral valve apparatus, the balloon is deflated and the arterial sheath 105 and the arterial sheath inner catheter 106 can be advanced across into the left ventricle. Generally, the surgeon can take care to position the arterial sheath inner catheter 106 and/or the guidewire using the inflated balloon to avoid any chordae tendineae.

Next, in FIG. 15E the distal tip of the arterial sheath inner catheter 106 is deflected until the distal tip of the arterial sheath inner catheter 106 is approximately centered with respect to the aortic valve. In some examples, the arterial sheath inner catheter 106 may be deflected more than about 140 degrees (e.g., more than 150 degrees, more than 160 degrees, more than 170 degrees, etc.). In other examples, the arterial sheath inner catheter 106 may be deflected by more than or less than 170 degrees. Deflection of the distal tip of the arterial sheath inner catheter 106 may be performed by moving a pull wire with a lever on a handle.

Next, in FIG. 15F, a stiff guidewire may be introduced into the catheter-based ECMO system 100 and advanced antegrade through the left ventricle output tract and across the aortic valve, up the ascending aorta, and down the descending aorta. In some examples, the guidewire can be stiffer than the guidewire used earlier in FIGS. 15A-15D.

Figure 15I:
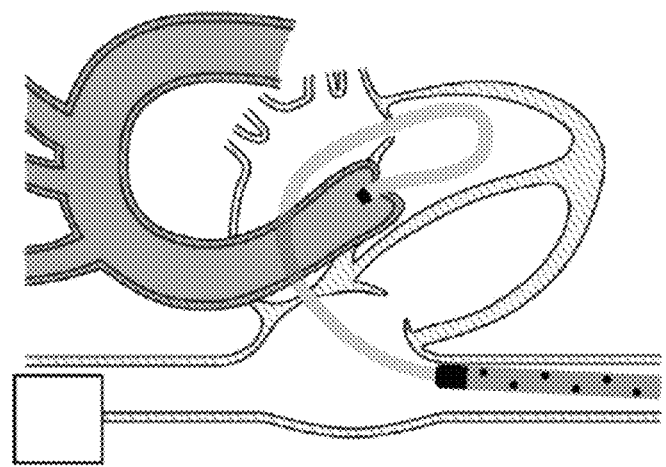
Figure 15H:
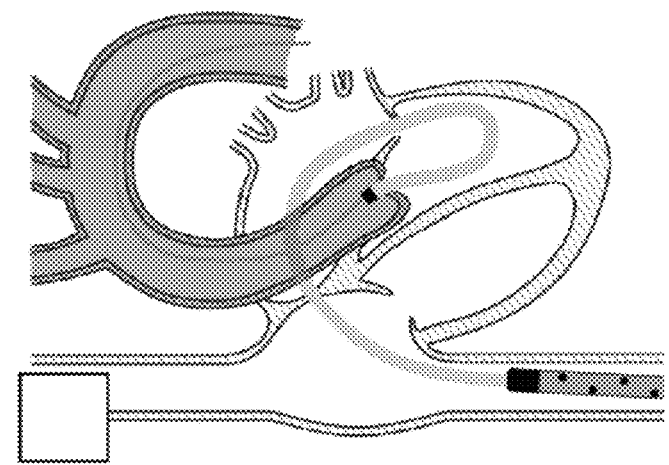
Figure 15G:
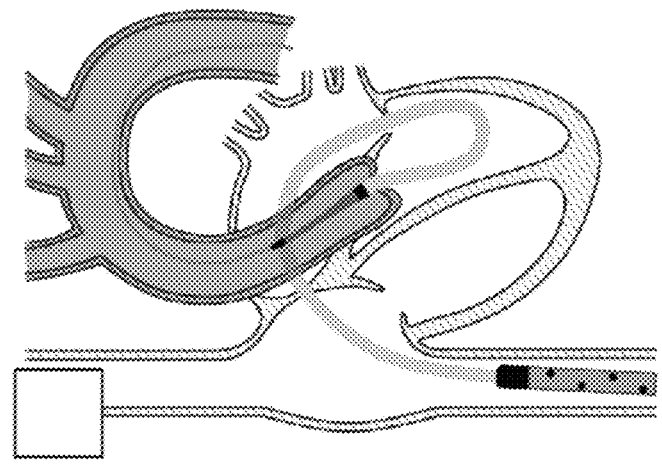

Next, in FIG. 15G, the arterial sheath 105 and the arterial sheath inner catheter 106 can be advanced over the guidewire until the tip of the arterial sheath 105 crosses the aortic valve and is positioned within the ascending aorta.

Next, in FIG. 15H, the arterial sheath inner catheter 106 is completely withdrawn from the catheter-based ECMO system 100. In FIG. 15I the guidewire is removed. The catheter-based ECMO system 100 is now in position to remove oxygen-poor blood through the venous sheath 110 and return blood through the arterial sheath 105.

Figure 16B:
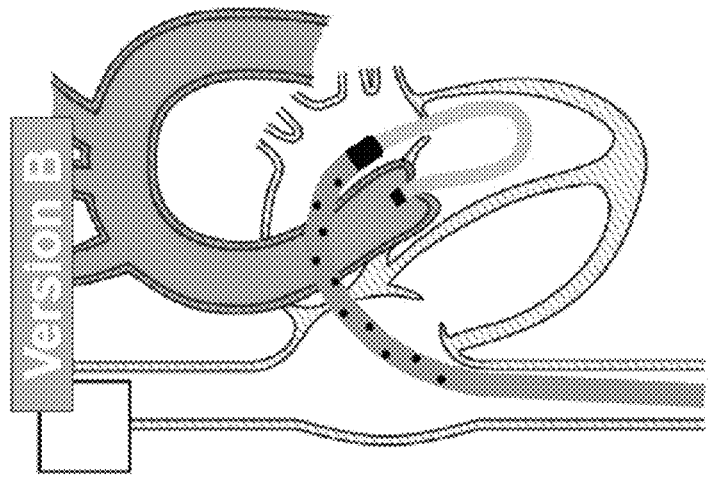
FIGS. 16A and 16B show possible configurations of a venous sheath and an arterial sheath for performing ECMO.
Figure 16A:
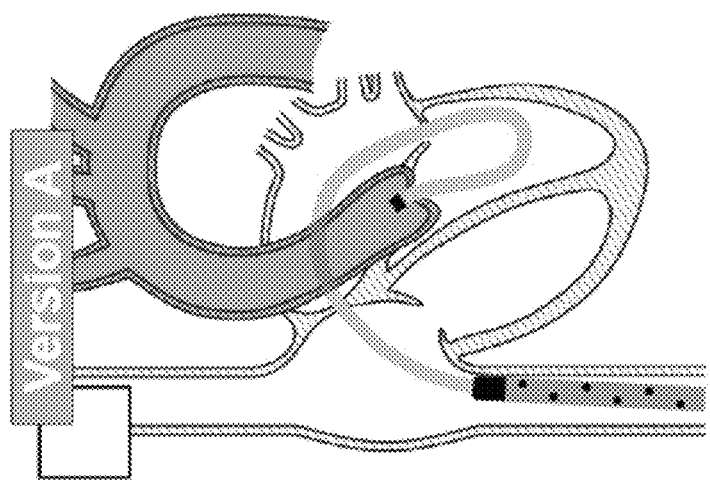

FIGS. 16A and 16B show possible configurations of the venous sheath 110 and the arterial sheath 105 for performing ECMO. In FIG. 16A, the venous sheath 110 is positioned within the inferior vena cava with the arterial sheath positioned across the aortic valve. FIG. 16B shows an alternative configuration where the venous sheath may be positioned across the septum and side-holes are within the left atrium and the right atrium to allow "decompression" and volume reduction for the heart left and/or right sided chambers. In either configuration, oxygenated blood may easily be exchanged for oxygen poor blood in a percutaneous manner with a single-entry point into the patient.

In some cases, a slightly different approach may be used to perform ECMO for a patient. For example, a catheter-based ECMO system may include two separate catheters: a venous sheath to remove blood and an arterial sheath to return blood. In general, the arterial sheath can include the arterial sheath 105 and the arterial sheath inner catheter 106 of the catheter-based catheter system 100. The venous sheath can be a single catheter that simply includes the venous sheath 110 of FIG. 1. This approach may allow larger (bigger cross-sectional catheter areas) to allow greater blood flow from the pump. In this manner, a first catheter can be used for removing blood and a second (separate) catheter can be used to return blood to the patient. Example steps for using this alternative catheter-based ECMO system is described with respect to FIGS. 17A-17I.

FIGS. 17A-17I show example steps of using a two catheter-based ECMO system. The steps described herein are merely exemplary and are not meant to be limiting. Other steps may be used, and in some cases, these steps may be performed in a different order. A first catheter can be a catheter that supports venous sheath functionality (performs operations of the venous sheath 110 of FIG. 1). A second catheter can be a catheter that supports arterial sheath and arterial sheath inner catheter functionality (performs operations of the arterial sheath 105 and the arterial sheath 105 of FIG. 1.)

Figure 17C:
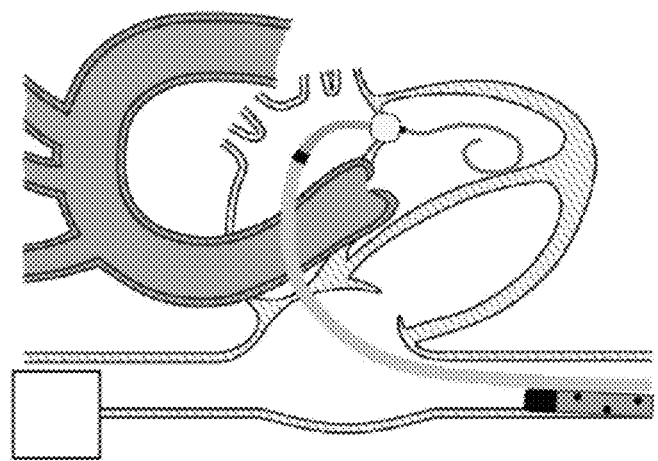
FIGS. 17A-17I show example steps of using a two catheter-based ECMO system.
Figure 17B:
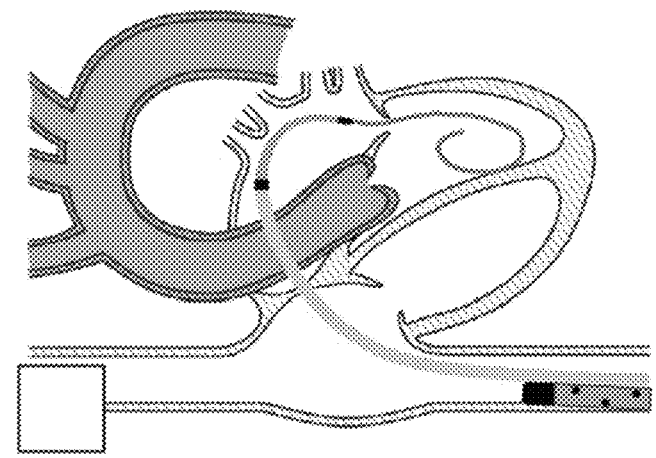
Figure 17A:
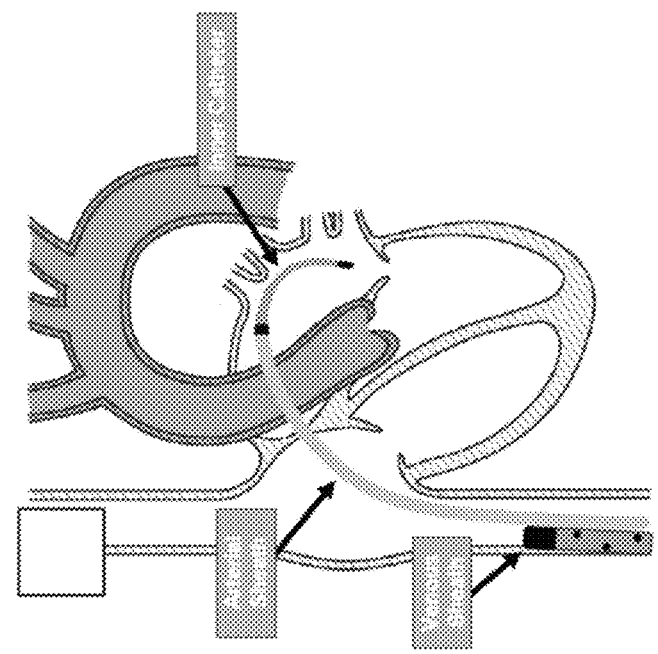

First, in FIG. 17A the arterial sheath and the arterial sheath inner catheter are advanced over a guidewire and through the atrial septum. Also, a separate venous sheath is advanced to the inferior vena cava.

Next, in FIG. 17B a floppy guidewire may be advanced into the left ventricle.

Next, in FIG. 17C, the arterial sheath 105 and the arterial sheath inner catheter may be advanced toward the mitral valve. The balloon may be positioned across the mitral valve and inflated. In this manner, the arterial sheath inner catheter may be advanced across the mitral valve.

Figure 17F:
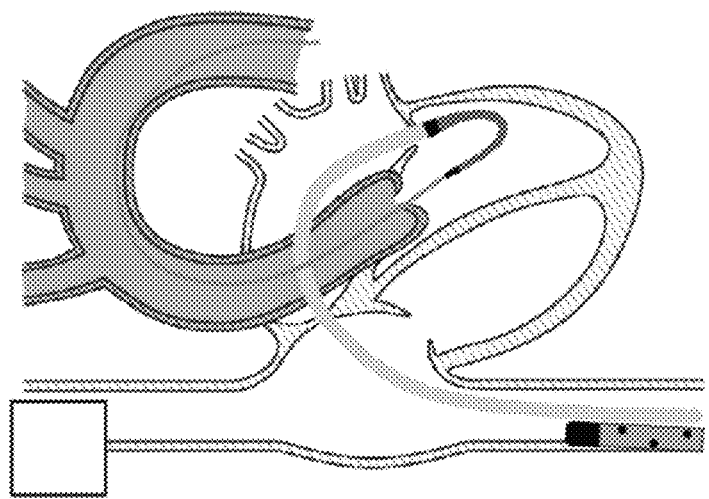
Figure 17E:
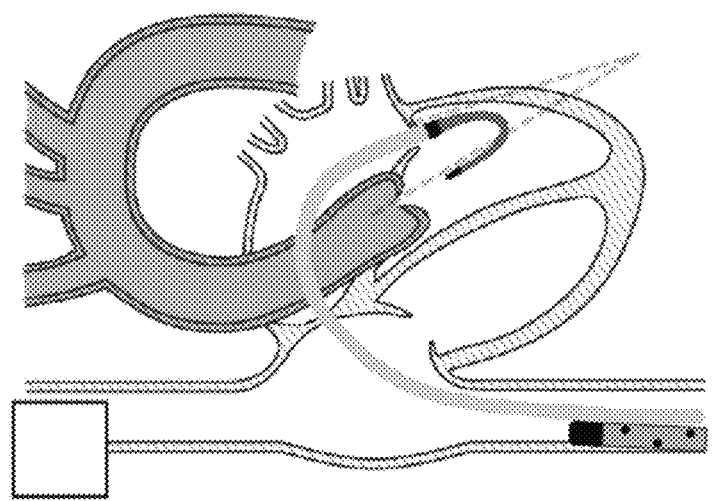
Figure 17D:
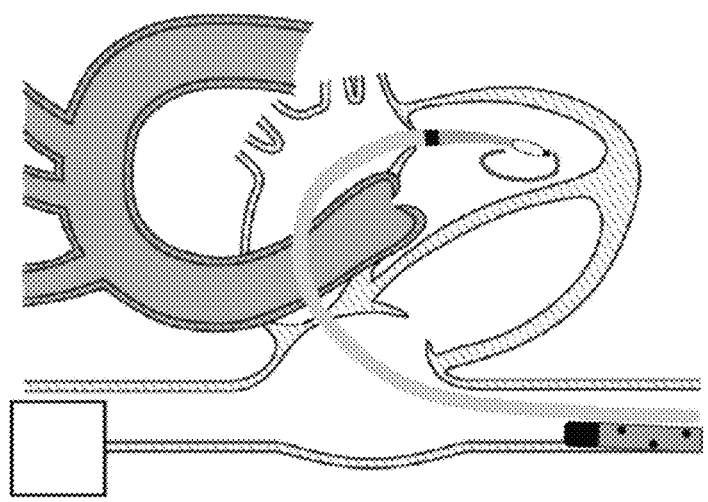
Figure 17I:
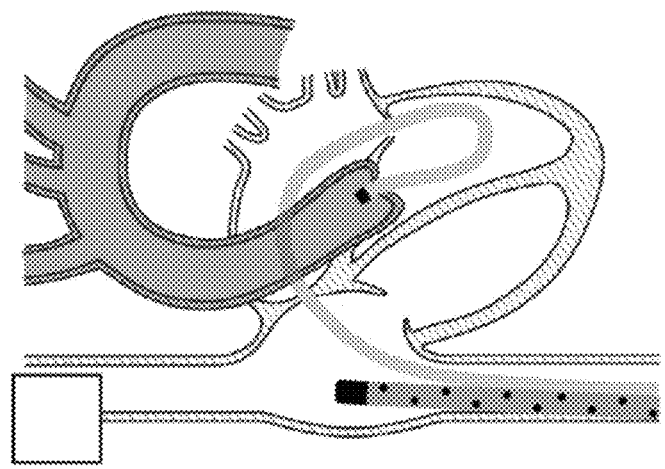

Next, in FIG. 17D, the balloon is inflated and the arterial sheath and the arterial sheath inner catheter can be advanced across the mitral valve into the left ventricle.

Next, in FIG. 17E, after balloon deflation, the distal tip of the arterial sheath inner catheter is deflected until approximately centered with respect to the aortic valve. In some examples, the arterial sheath inner catheter may be deflected by between about 140-190 degrees (e.g., 170 degrees).

Next, in FIG. 17F, a stiff guidewire may be introduced into the catheter-based ECMO system and advanced antegrade through the left ventricle output tract and across the aortic valve, up the ascending aorta, and down the descending aorta.

Figure 17H:
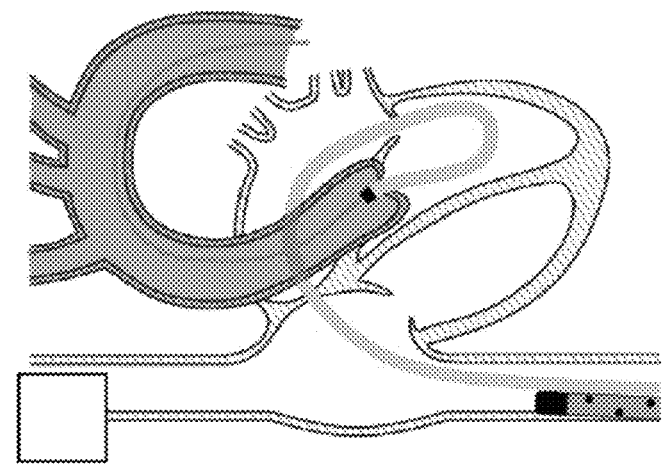
Figure 17G:
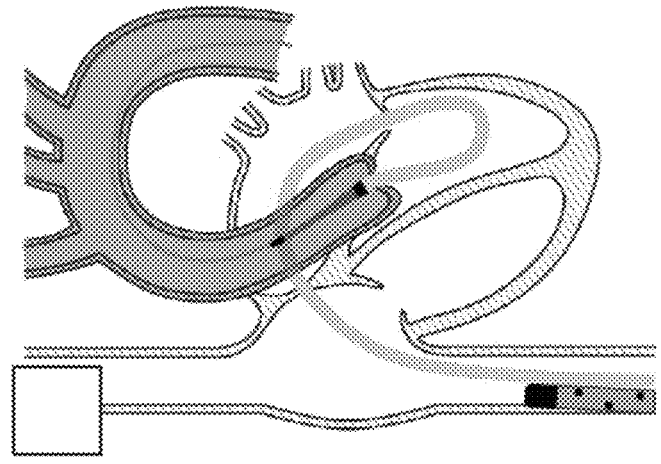

Next, in FIG. 17G the arterial sheath and the arterial sheath inner catheter can be advanced over the guidewire until the tip of the arterial sheath crosses the aortic valve and is positioned within the ascending aorta.

Next, in FIG. 17H, the arterial sheath inner catheter is completely withdrawn. Next, in FIG. 17I, the guidewire is withdrawn and the venous sheath can be positioned within the inferior vena cava. Notably, the example steps of FIG. 17A-FIG. 17I may be similar to steps described with respect to FIG. 15A-FIG. 15I, particularly due to the similarly of the functions of the arterial sheaths and the arterial sheath inner catheters used in both examples.

Figure 18:
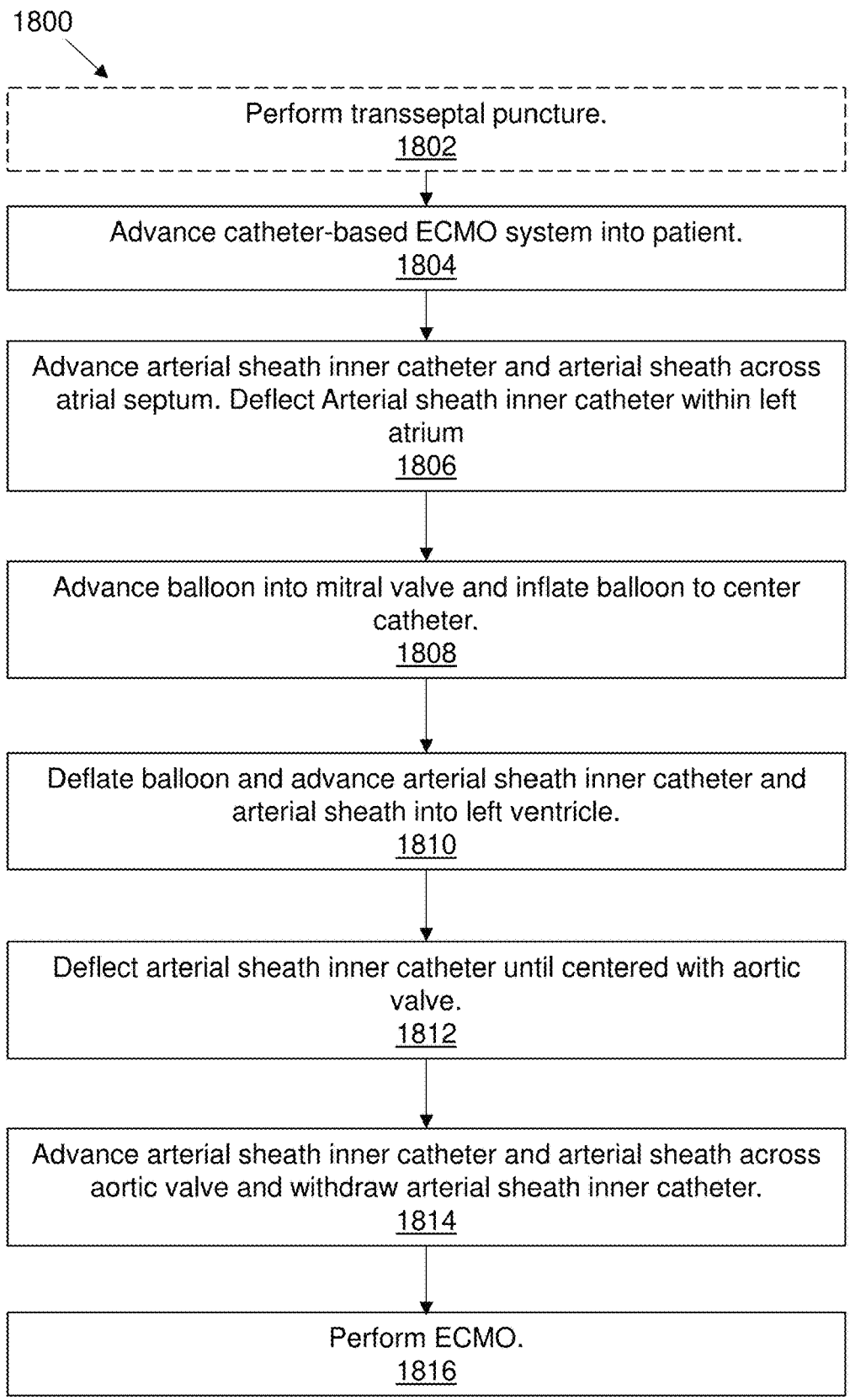
FIG. 18 is a flowchart showing an example method for performing ECMO with the catheter-based ECMO system of FIG. 1.

FIG. 18 is a flowchart showing an example method 1800 for performing ECMO with a catheter-based ECMO system. Some examples may perform the operations described herein with additional operations, fewer operations, operations in a different order, operations in parallel, and some operations differently. The method 1800 is described below with respect to the catheter-based ECMO system 100 of FIG. 1, however, the method 1800 may be performed by any other suitable system or device.

The method 1800 begins in block 1802 as a transeptal puncture is performed. In some examples, this operation may be optional, as indicated here by dashed lines. The transeptal puncture may be performed by a distal end of the catheter-based ECMO system 100, or any other feasible device.

Next, in block 1804 a catheter-based ECMO system is advanced into the patient. For example, the catheter-based ECMO system 100 may be inserted percutaneously into a femoral vein of the patient. The catheter-based ECMO system 100 may include a venous sheath 110, an arterial sheath 105, and an arterial sheath inner catheter 106.

Next, in block 1806, the arterial sheath inner catheter and the arterial sheath is advanced across the atrial septum. In addition, the arterial sheath inner catheter 106 is deflected within the left atrium. In some examples, the venous sheath 110 may be positioned within the inferior vena cava. Operations of block 1806 may be further described above with respect to FIG. 15A and FIG. 15B. Any of these apparatuses may include an outer member 110, e.g., sheath or venus sheath, that includes a plurality of openings (holes, gaps, windows, etc.) to allow inflow of un-oxygenated blood that may be removed, oxygenated, and returned through an inner catheter that is placed with a distal end in the ascending aortic arch, as described herein.

Next, in block 1808, a balloon is advanced and inflated within the mitral valve to center the catheter. For example, the balloon 201 of FIG. 2, may be inflated through the handle 125. Operations of block 1808 may be further described above with respect to FIG. 15C.

Next, in block 1810 the balloon is deflated and the arterial sheath and the arterial sheath inner catheter is advanced into the left ventricle. For example, the arterial sheath 105 and the arterial sheath inner catheter 106 may be advanced into the left ventricle. The operations of block 1810 may be further described above with respect to FIG. 15D.

Next, in block 1812 the arterial sheath inner catheter is deflected until centered with respect to the aortic valve. For example, the arterial sheath inner catheter 106 of the catheter-based ECMO system 100 is deflected until a distal tip of the arterial sheath inner catheter 106 is pointed toward the center of the aortic valve. The operations of block 1812 may be further described above with respect to FIG. 15E.

Next, in block 1814 the arterial sheath inner catheter and the arterial sheath are advanced across the aortic valve and then the arterial sheath inner catheter is withdrawn. For example, the arterial sheath inner catheter 106 and the arterial sheath 105 are advanced across the aortic valve. After this advancement, the arterial sheath inner catheter 106 can be withdrawn from at least the arterial sheath 105. The operations of block 1814 may be further described with respect to FIGS. 15F-15I.

Next, in block 1816 ECMO is performed.

Figure 19:
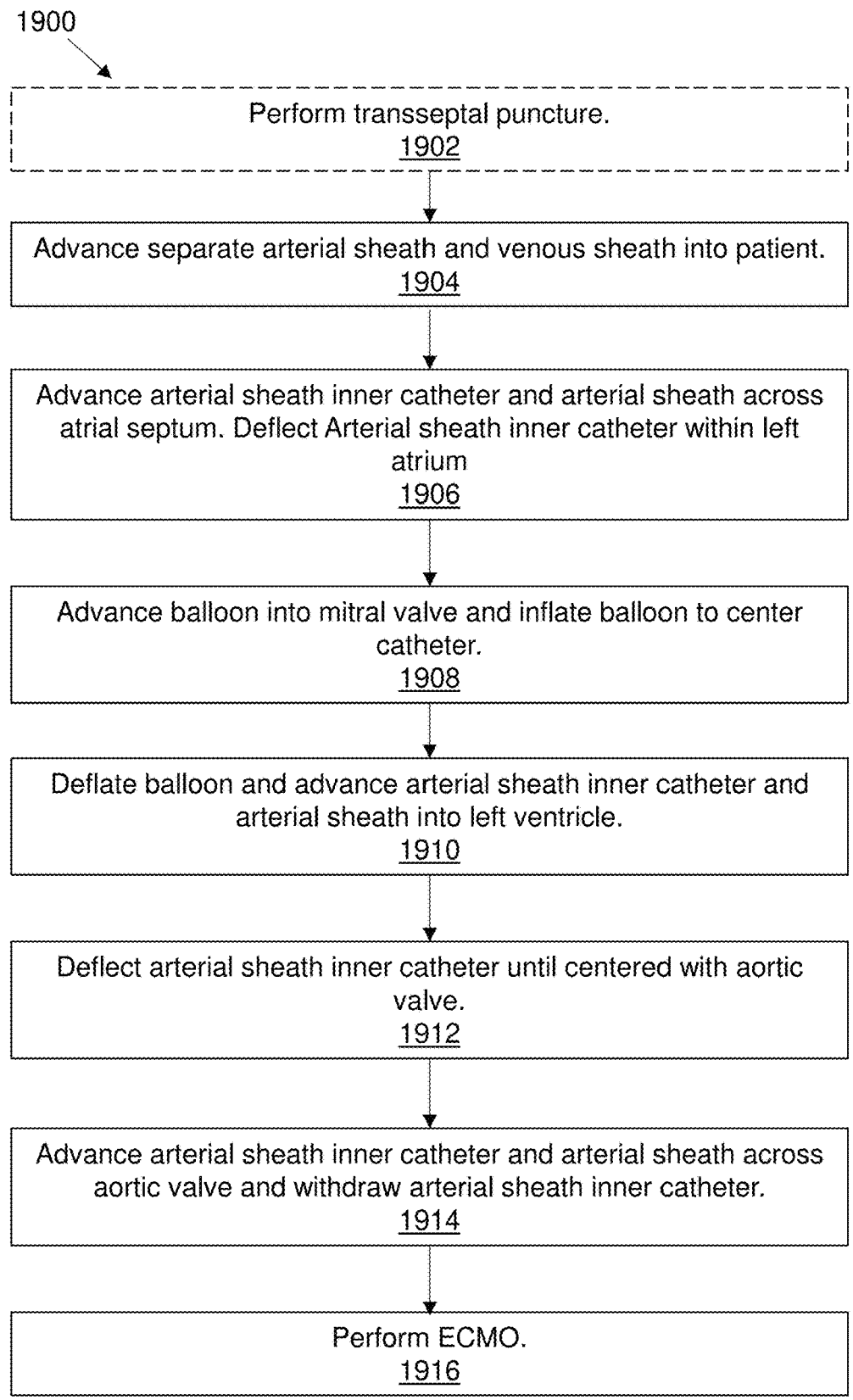
FIG. 19 is a flowchart showing an example method for performing ECMO with a two catheter-based ECMO system.

FIG. 19 is a flowchart showing an example method 1900 for performing ECMO with a two catheter-based ECMO system. Such a system may include a first catheter that removes blood from the patient and a second catheter that returns blood to the patient. The first catheter can include a venous sheath, similar to the venous sheath 110 of FIG. 1. The second catheter can include an arterial sheath and an arterial sheath inner catheter, similar to the arterial sheath 105 and the arterial sheath inner catheter 106 of FIG. 1.

The method 1900 begins in block 1902 as a transeptal puncture is performed. In some examples, this operation may be optional, as indicated here by dashed lines.

Next, in block 1904 an venous sheath may be advanced into the patient. Also, an arterial sheath and an arterial sheath inner catheter may be advanced into the patient. In some examples, the venous sheath may be advanced through a first femoral artery while the arterial sheath and arterial sheath inner catheter may be advanced through a second femoral artery.

Next, in block 1906, the arterial sheath inner catheter and the arterial sheath is advanced across the atrial septum. In addition, the arterial sheath inner catheter is deflected within the left atrium. The venous sheath may be positioned in the inferior vena cava. Operations of block 1906 may be further described above with respect to FIG. 17A and FIG. 17B.

Next, in block 1908, a balloon is advanced and inflated within the mitral valve to center the catheter. Operations of block 1908 may be further described above with respect to FIG. 17C.

Next, in block 1910 the balloon is deflated and the arterial sheath and the arterial sheath inner catheter is advanced into the left ventricle. The operations of block 1910 may be further described above with respect to FIG. 17D.

Next, in block 1912 the arterial sheath inner catheter is deflected until centered with respect to the aortic valve. For example, the arterial sheath inner catheter is deflected until a distal tip of the arterial sheath inner catheter is pointed toward the center of the aortic valve. The operations of block 1912 may be described above with respect to FIG. 17E.

Next, in block 1914 the arterial sheath inner catheter and the arterial sheath are advanced across the aortic valve and then the arterial sheath inner catheter is withdrawn. After this advancement, the arterial sheath inner catheter can be withdrawn from at least the arterial sheath 105. The operations of block 1914 may be further described with respect to FIGS. 17F-17I.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for performing transseptal extracorporeal membrane oxygenation (ECMO) on a patient, the method comprising:
   advancing a first inner catheter that is distally tapered and a second inner catheter through a transseptal puncture, wherein the second inner catheter is coaxial with and surrounds the first inner catheter and an outer surface of the second inner catheter is flush with an outer surface of the first inner catheter;
   deflecting the first inner catheter within the left atrium so that a distal tip of the first inner catheter is disposed substantially toward a mitral valve;
   advancing the first inner catheter and the second inner catheter through the mitral valve;
   deflecting the distal tip of the first inner catheter toward an aortic valve;
   advancing the first inner catheter and the second inner catheter through the aortic valve so that a distal end of the second inner catheter is in an ascending aorta;
   withdrawing the first inner catheter; and
   receiving, from the patient, oxygen-poor blood through an outer catheter and returning oxygenated blood through the second inner catheter to the ascending aortic arch.

2. The method of claim 1, wherein the outer catheter surrounds the second inner catheter.

3. The method of claim 1, further comprising inflating a balloon disposed around a distal end of the first inner catheter to center the first inner catheter with respect to the mitral valve.

4. The method of claim 3, further comprising deflating the balloon after advancing the first inner catheter and the second inner catheter through the mitral valve.

5. The method of claim 1, wherein deflecting the distal tip of the first inner catheter toward the aortic valve comprises deflecting the distal tip by more than 140 degrees with respect to a proximal section of the first inner catheter.

6. The method of claim 1, wherein the second inner catheter includes a plurality of holes disposed around a body of the second inner catheter to return the oxygenated blood.

7. The method of claim 1, wherein the outer catheter includes a plurality of holes disposed around a body of the outer catheter to receive the oxygen-poor blood.

8. The method of claim 1, further comprising:
   inserting a first guidewire through the first inner catheter, the second inner catheter, and the outer catheter prior to deflecting the first inner catheter within the left atrium.

9. The method of claim 8, further comprising:
   withdrawing the first guidewire prior to deflecting the distal tip of the first inner catheter toward the aortic valve; and
   inserting a second guidewire stiffer than the first guidewire, after withdrawing the first guidewire.

10. The method of claim 1, further comprising:
    puncturing a septum between the right atrium and the left atrium before advancing the first inner catheter and the second inner catheter through the transseptal puncture.

11. A method for performing transseptal extracorporeal membrane oxygenation (ECMO) on a patient, the method comprising:
    advancing a first catheter that includes an inner sheath and an outer sheath through a transseptal puncture, wherein the outer sheath is coaxial with and surrounds the inner sheath and an outer surface of the outer sheath is flush with an outer surface of the inner sheath;
    advancing a second catheter into a large peripheral vein or an inferior vena cava;
    deflecting the inner sheath within the left atrium so that a distal tip of the inner sheath is disposed substantially toward a mitral valve;
    advancing the inner sheath through the mitral valve;
    deflecting the distal tip of the inner sheath toward an aortic valve;
    advancing the first catheter through the aortic valve and into an ascending aorta;
    withdrawing the inner sheath from the first catheter; and
    receiving, from the patient, oxygen-poor blood through the second catheter and returning oxygenated blood through the first catheter into the ascending aorta.

12. The method of claim 11, further comprising inflating a balloon disposed around a distal end of the inner sheath to center the inner sheath with respect to the mitral valve.

13. The method of claim 12, further comprising deflating the balloon after advancing the inner sheath and the outer sheath through the mitral valve.

14. The method of claim 11, wherein deflecting the distal tip of the inner sheath toward an aortic valve comprises deflecting the distal tip by more than 140 degrees with respect to a proximal section of the inner sheath.

15. The method of claim 11, wherein the second catheter includes a plurality of holes disposed around a body of the second catheter to return the oxygenated blood.

16. The method of claim 11, wherein the outer sheath includes a plurality of holes disposed around a body of the outer sheath to receive the oxygen-poor blood.

17. The method of claim 11, further comprising:
    inserting a first guidewire through the inner sheath and the outer sheath prior to deflecting the inner sheath within the left atrium.

18. The method of claim 17, further comprising:
    withdrawing the first guidewire prior to deflecting the distal tip of the inner sheath toward the aortic valve; and
    inserting a second guidewire stiffer than the first guidewire, after withdrawing the first guidewire.

19. The method of claim 11, further comprising:
    puncturing a septum between the right atrium and the left atrium before advancing the inner sheath and the outer sheath through the transseptal puncture.

* * * * *